(12) United States Patent
Sohn et al.

(10) Patent No.: US 12,187,672 B2
(45) Date of Patent: Jan. 7, 2025

(54) 1,2-DIACYLGLYCEROL COMPOUND, PREPARATION METHOD THEREFOR, AND IMMUNOMODULATOR CONTAINING SAME AS ACTIVE INGREDIENT

(71) Applicant: ENZYCHEM LIFESCIENCES CORPORATION, Jecheon-si (KR)

(72) Inventors: Ki Young Sohn, Seoul (KR); Jae Wha Kim, Daejeon (KR); Sun Young Yoon, Daejeon (KR); Chang Hyun Yoo, Daejeon (KR); Jin Seon Jeong, Cheonan-si (KR)

(73) Assignee: ENZYCHEM LIFESCIENCES CORPORATION, Jecheon-si (KR)

( * ) Notice: Subject to any disclaimer, the term of this patent is extended or adjusted under 35 U.S.C. 154(b) by 998 days.

(21) Appl. No.: 16/978,873

(22) PCT Filed: Mar. 25, 2019

(86) PCT No.: PCT/KR2019/003437
§ 371 (c)(1),
(2) Date: Sep. 8, 2020

(87) PCT Pub. No.: WO2019/190137
PCT Pub. Date: Oct. 3, 2019

(65) Prior Publication Data
US 2021/0002197 A1 Jan. 7, 2021

(30) Foreign Application Priority Data
Mar. 26, 2018 (KR) .......................... 10-2018-0034537

(51) Int. Cl.
| | | |
|---|---|---|
| *C07C 41/09* | (2006.01) | |
| *A23L 33/115* | (2016.01) | |
| *A61K 31/22* | (2006.01) | |
| *A61K 31/23* | (2006.01) | |
| *A61P 31/00* | (2006.01) | |
| *A61P 37/00* | (2006.01) | |
| *A61P 37/02* | (2006.01) | |
| *C07C 69/30* | (2006.01) | |
| *C07C 69/587* | (2006.01) | |

(52) U.S. Cl.
CPC .............. *C07C 41/09* (2013.01); *A61P 37/02* (2018.01)

(58) Field of Classification Search
CPC ....... A61K 31/23; A61K 31/22; A23L 33/115; C07C 69/30; C07C 69/587; C07C 67/29; C07C 67/14; C07C 67/08; C07C 67/26; C07C 69/78; A61P 37/02; A61P 31/00; A61P 37/00; A23V 2002/00; A23V 2200/324
See application file for complete search history.

(56) References Cited

U.S. PATENT DOCUMENTS

| | | |
|---|---|---|
| 2004/0147599 A1 | 7/2004 | Gagnon et al. |
| 2008/0194684 A1 | 8/2008 | Harbige et al. |
| 2009/0131523 A1* | 5/2009 | Yosef ..................... A61K 31/20 426/2 |
| 2010/0137435 A1 | 6/2010 | Kim |
| 2022/0339135 A1* | 10/2022 | Kim ....................... A61P 29/00 |

FOREIGN PATENT DOCUMENTS

| | | | |
|---|---|---|---|
| CA | 2081119 | 10/1991 | |
| EP | 1 900 364 | 3/2008 | |
| EP | 2 324 828 | 5/2011 | |
| JP | 1993-506661 | 9/1993 | |
| JP | 2007-502805 | 2/2007 | |
| KR | 10-2003-0096323 | 12/2003 | |
| KR | 10-2006-0047447 | 5/2006 | |
| WO | 2005/112912 | 12/2005 | |
| WO | WO-2005112912 A1 * | 12/2005 | ............... A21D 2/16 |
| WO | 2013/052252 | 4/2013 | |

OTHER PUBLICATIONS

P. Villeneuve et al., "Chiral synthesis of a triglyceride: example of 1-butyroyl 2-oleoyl 3-palmitoyl sn glycerol", Chemistry and Physics of Lipids, vol. 72, Issue 2, Aug. 8, 1994, pp. 135-141. (Year: 1994).*
Frieri, M., Krishan Kumar and A. Boutin, "Antibiotic resistance", Journal of Infection and Public Health (2017), 10: pp. 369-378. (Year: 2017).*
Kalo, P., A. Kemppinen and V. Ollilainen, "Determination of Triacylglycerols in Butterfat by Normal-Phase HPLC and Electrospray-Tandem Mass Spectrometry", Lipids (2009), 44: 169-195. (Year: 2009).*
CAS Registry No. 1183880-94-5 of Kalo, P., A. Kemppinen and V. Ollilainen, "Determination of Triacylglycerols in Butterfat by Normal-Phase HPLC and Electrospray-Tandem Mass Spectrometry", Lipids (2009), 44: 169-195. (Year: 2009).*
CAS Registry No. 1183880-94-5 (Entered STN date: Sep. 14, 2009). (Year: 2009).*
Ganong, B., C. Loomis, Y. Hannun and R. Bell, "Specificity and mechanism of protein kinase C activation by sn-1,2-diacylglycerols", Proc. Natl. Acad. Sci. (1986), 83: pp. 1184-1188. (Year: 1986).*

(Continued)

*Primary Examiner* — Amanda L. Aguirre
*Assistant Examiner* — Sagar Patel
(74) *Attorney, Agent, or Firm* — LEX IP MEISTER, PLLC

(57) ABSTRACT

Disclosed are a novel 1,2-diacylglycerol compound that useful for improving, preventing or treating inflammation-related diseases by inhibiting overexpression of various inflammatory cytokines such as IL-4 and IL-6 or chemokine CXCL8 related to the migration of inflammatory cells, a method for preparing the same, and an immunomodulator containing the same as an active ingredient. The 1,2-diacylglycerol compound is represented by Chemical Formula 2 in the patent specification.

10 Claims, 6 Drawing Sheets

(56) References Cited

OTHER PUBLICATIONS

CAS Registry No. 958830-64-3 (Entered STN date: Dec. 19, 2007). (Year: 2007).*

Muller, C., B. Kanawati, T. Rock, S. Forcisi, F. Moritz and P. Schmitt-Kopplin, "Dimer ion format. and intermol. fragment. of 1,2-diacylglycerols revealed by electrospray ionization Fourier transform ion cyclotron resonance mass spectr.", Rapid Commun. Mass Spectrom. (2014), 28: pp. 1735-1744. (Year: 2014).*

Popovic, M.; Prostenik, M., Synthesis of L (+)-1- (O-ethyl) glycerol, Bulletin Scientifique, Section A: Sciences Naturelles, Techniques et Me dicales (Zagreb) 1973, 18 (7-9), pp. 129-130.

EPO, Search Report of EP 19774283.6 dated Oct. 14, 2021.

Josie C. Briggs et al., "Synthesis of diacylglycerol analogues as potential second messenger antagonists and inhibitors of protein kinase C", Carbohydrate Research, vol. 234, Oct. 9, 1992, 23-35.

R. Aneja et al., "Nucleophilic Substitution in Glycerol Derivatives, Part II: Unsymmetrical Dioxolenium Ions as Intermediates in the Re, Actions of Diacylglycerosulphonates With Carboxylate Ions", Tetrahedron Letters, 1972, pp. 4497-4500.

Jonas Blomberg, "Unusual Lipids II: Head Oil of the North Atlantic Pilot Whale, Globicephala melaena melaena", LIPIDS, vol. 9, No. 7, Jul. 1, 1974, pp. 461-470.

P. Kalo et al., "Analysis of regioisomers of short-chain triacylglycerols by normal phase liquid chromatography-electrospray tandem mass spectrometry", International Journal of Mass Spectrometry, vol. 229, No. 3, Oct. 2003, pp. 167-180.

Marcel S.F. Lie Ken Jie et al., "H-Nuclear magnetic resonance spectroscopic studies of saturated, acetylenic and ethylenic triacylglycerols", Chemistry and Physics of Lipids, vol. 77, No. 2, 1995, pp. 155-171.

C.M. Lok et al., "The Synthesis of Chiral Glycerides Starting From D- and L-Serine", Chemistry and Physics of Lipids, vol. 16, No. 2, Mar. 1976, pp. 115-122.

Database Reaxys [Online] Elsevier Life Sciences IP Limited; Jan. 1, 1929 (Jan. 1, 1929), Anonymous: "1-glycyloxy-2, 3-bis-palmitoyloxy-propane and 1-glycyloxy-2,3-bis-stearoyloxy-propane", XP055847316, Database accession No. 1810598, 1810877 (RID) (abstract).

Robert T. O'Connor et al., "The Infrared :Spectra of Mono-, Di-, and Triglycerides", Journal of the American Oil Chemists Society, vol. 32, No. 2, Feb. 1, 1955, pp. 88-93.

Jun-ichi Nagata et al., "Effects of Highly Purified Structured Lipids Containing Medium-chain Fatty Acids and Linoleic Acid on Lipid Profiles in Rats", Biosci. Biotechnol. Biochem., vol. 67, Jan. 1, 2003, pp. 1937-1943.

Anand Swaroop et al., "Isolation and Characterization of 1,3-Dicapryloyl-2-linoleoylglycerol: A Novel Triglyceride from Berries of Hippophae rhamnoides", Chem. Pharm. Bull., vol. 53, No. 8, Jan. 1, 2005, pp. 1021-1024.

Database CA [Online] Chemical Abstracts Service, Columbus, Ohio, US; 1996, Vodovozova et al.: "Lipid Derivatives of Sarcolysine, Methotrexate, and Rubomycin", XP055847735, retrieved from STN Database accession No. 1996:716536 Abstract; RN 184883-29-2. & Bioorganicheskaya Khimiya (1996), 22(7), 548-556.

Database CA [Online] Chemical Abstracts Service, Columbus, Ohio, US; Michelsen, Peter et al: "Synthesis and chiroptical properties of neutral ether lipids", XP055847746, retrieved from STN Database accession No. 1983:422811 Abstract; RN 86158-17-0. & Chemistry and Physics of Lipids (1983), 32(1). 27-37.

Database CA [Online] Chemical Abstracts Service, Columbus, Ohio, US; Popovic et al.: "Synthesis of L(+)-1-(0-ethyl)glycerols", XP055847751, retrieved from STN Database accession No. 1974:3025 Abstract; RNs 50598-10-2, 50598-11-3, 50598-12-4, 50598-13-5. & Bulletin Scientifique, Section A: Sciences Naturelles, Techniques et Medicales (Zagreb) (1973), 18(7-9), 129-30.

KIPO, PCT Search Report of PCT/KR2019/003437 dated Jul. 23, 2019.

P.Villeneuve et al., "Chiral synthesis of a triglyceride: example of 1-butyroyl 2-oleoyl 3-palmitoyl sn glycerol", Chemistry and Physics of Lipids, vol. 72, Issue 2, Aug. 8, 1994, pp. 135-141.

Kenji Mori, "Pheromone synthesis. Part 253: Synthesis of the racemates and enantiomers of triglycerides of male *Drosophila* fruit flies with special emphasis on the preparation of enantiomerically pure 1-monoglycerides", Tetrahedron 68 (2012) 8441-8449. http://dx.doi.org/10.1016/j.tet.2012.07.086.

A.P.J. Mank et al., "A Versatile, Flexible Synthesis of 1,3-Diglycerides and Triglycerides", Chemistry and Physics of Lipids 16 (1976) 107-114.

KIPO, PCT International Preliminary Report on Patentability of PCT/KR2019/003437 dated Sep. 29, 2020.

Intellectual Property India, Indian Examination Report for IN 202027038438 dated Nov. 24, 2020.

* cited by examiner

1,2-DIACYLGLYCEROL COMPOUND, PREPARATION METHOD THEREFOR, AND IMMUNOMODULATOR CONTAINING SAME AS ACTIVE INGREDIENT

TECHNICAL FIELD

The present invention relates to a 1,2-diacylglycerol compound, and more particularly, to a novel 1,2-diacylglycerol compound useful for improvement, prevention or treatment of inflammation related diseases, a method for preparing the same, and an immunomodulator containing the same as an active ingredient, which inhibits overexpression of various inflammatory cytokines, such as IL-4, IL-6 and so on, or CXCL8 which is a chemokine involved in the migration of inflammatory cells.

BACKGROUND ART

Immunity is a defense of a living body from various pathogens, and immunodeficiency means an occurrence of defects in some components of an immune system. As a result, immune response may not occur for many types of antigens. These immune deficiencies are largely classified into a congenital or primary immunodeficiency and an acquired or secondary immunodeficiency. The congenital immunodeficiency is that in which immune cells such as B cells and T cells do not exist originally, and a treatment of the congenital immunodeficiency can be done only by gene therapy, antibody injection, or bone marrow transplantation. On the other hand, the acquired immunodeficiency syndrome is that in which the immune components exists originally, but the immune response of them abnormally occurs. The immunodeficiency due to the acquired immunodeficiency syndrome can be improved by enhancing the function of the immune components.

Recently, there are many immune diseases that occur due to an abnormal increase in immune function. These immune diseases are mainly treated by using immunosuppressants. However, when using an immunosuppressant, the body's overall immunity is also lowered, causing other problems in many cases. Recently, as the action mechanism of immune function is researched, immunomodulatory substances that can enhance or suppress immune function are being developed world widely.

The target of such research is to stimulate immune cells with the immunomodulatory substance to enhance or suppress the body's immune function, thereby enhancing the body's defense ability from foreign disease factors and at the same time minimizing side effects caused by overexpression of the immune function. As such immunomodulatory substance, Korean Patent Publication No. 10-2006-0047447 discloses a monoacetyldiacylglycerol compound represented by the following Formula 1. The compound represented by the Formula 1 is 1-palmitoyl-2-linoleoyl-3-acetylglycerol, and is commonly known as EC-18 or PLAG.

[Chemical formula 1]

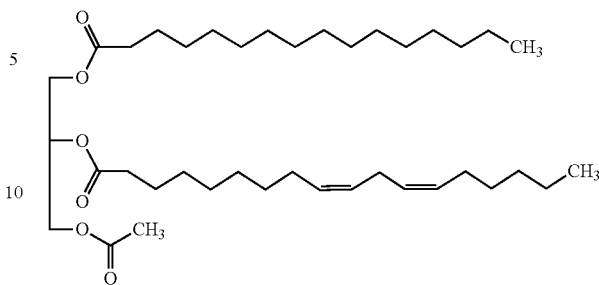

The compound of Formula 1 is known to be effective in not only preventing and treating diseases caused by the decline of various immune functions and various cancers, but also inhibiting, preventing and treating cell damages (autoimmune diseases) due to autoimmune effects such as arthritis, atopic, dementia, or sepsis.

DISCLOSURE OF INVENTION

An object of the present invention is to provide a novel 1,2-diacylglycerol compound and a method for preparing the same.

Other object of the present invention is to provide a novel 1,2-diacylglycerol compound having an immunomodulatory function similar to 1-palmitoyl-2-linoleoyl-3-acetylglycerol (EC-18), a conventional immunomodulatory substance and a method for preparing the same.

Another object of the present invention is to provide a novel 1,2-diacylglycerol compound for improving, preventing or treating inflammation-related diseases by inhibiting overexpression of various inflammatory cytokines such as IL-4, IL-6 and so on, or chemokine CXCL8 involved in the migration of inflammatory cells, and an immunomodulator containing the 1,2-diacylglycerol compound as an active ingredient.

For achieving the above objects, the present invention provides a 1,2-diacylglycerol compound represented by following formula 2.

[Chemical formula 2]

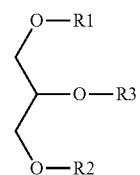

In Chemical formula 2, R1 is a fatty acid residue of 8 to 18 carbon atoms, and R3 is a fatty acid residue of 4 to 18 carbon atoms, and R2 is an alkyl group of 1 to 3 carbon atoms,

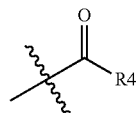

(R4 is an aliphatic or aromatic hydrocarbon group of 2 to 8 carbon atoms),

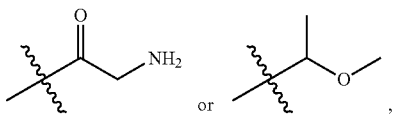

or , and ∿ represents a bonding portion.

In addition, the present invention provides an immunomodulator and a health functional food composition comprising the 1,2-diacylglycerol compound represented by Chemical formula 2 as an active ingredient. In addition, the present invention provides a method for regulating immunity comprising administering an immunomodulator containing the 1,2-diacylglycerol compound represented by Chemical formula 2 as an active ingredient to a non-human subject.

The novel 1,2-diacylglycerol compound of the present invention has an immunomodulatory function similar to 1-palmitoyl-2-linoleoyl-3-acetylglycerol (EC-18), a conventional immunomodulatory substance. By inhibiting overexpression of various inflammatory cytokines such as IL-4, IL-6, or IL-8, it can be usefully used for improving, preventing or treating of inflammation-related diseases.

BEST MODES FOR CARRYING OUT THE INVENTION

Figure 1:
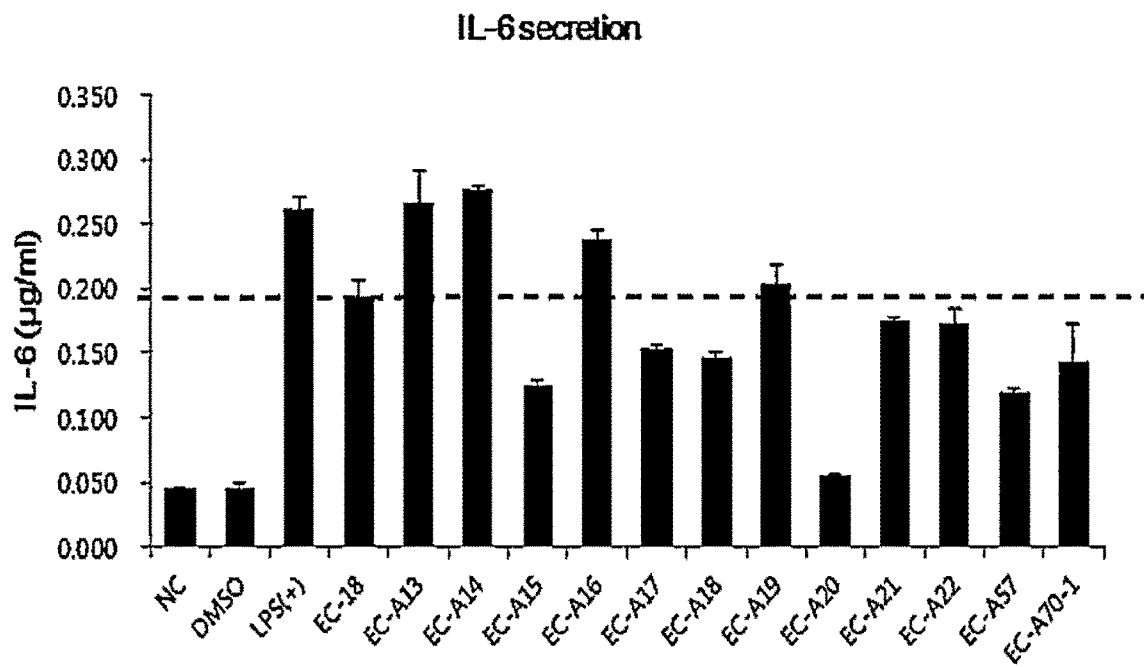
FIGS. 1 and 2 are graphs showing the effect of IL-6 secretion reduction of the conventional and diacylglycerol derivative compound according to the present invention.

Hereinafter, the present invention will be described in detail.

The present invention provides a novel 1,2-diacylglycerol compound represented by the following Chemical formula 2.

[Chemical formula 2]

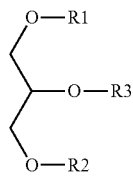

In Chemical formula 2, R1 is a fatty acid residue of 8 to 18 carbon atoms, and R3 is a fatty acid residue of 4 to 18 carbon atoms, and R2 is alkyl group of 1 to 3 carbon atoms,

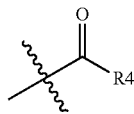

(R4 is an aliphatic or aromatic hydrocarbon group of 2 to 8 carbon atoms),

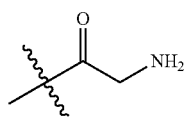

(2-Aminoacetyl) or

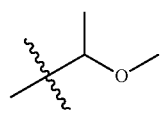 [SMILES: *C(C)OC]

(1-Methoxyethyl), and ∿ represents a bonding portion. In Chemical formula 2, the fatty acid residue refers to an acyl group in which a hydroxy group (—OH) has been removed from a chain or branched and saturated or unsaturated fatty acid. In Chemical formula 2, R1 may be a fatty acid residue of 8 to 16 carbon atoms, for example octanoyl, lauroyl, decanoyl, palmitoyl and so on. R3 may be butyryl, 2-methylbutyryl, pivaloyl, linoleoyl and so on. R2 may be a methyl group, an ethyl group, a propyl group, or an isopropyl group. R4 may be a chain, branched or cyclic and saturated or unsaturated aliphatic hydrocarbon group of 2 to 8 carbon atoms, or an aromatic group of 6 to 8 carbon atoms. For example, the cyclic saturated hydrocarbon group may be a cyclopropyl group, a cyclohexyl group, and so on, and the aromatic group may be phenyl group. The 1,2-diacylglycerol compound represented by Chemical formula 2 is a racemic or optically active compound. Preferred examples of the 1,2-diacylglycerol compound represented by Chemical formula 2 may include a compound in which R1 is palmitoyl, R2 is 2-methylbutyryl, R3 is linoleoyl (hereinafter, EC-A20), or R1 is palmitoyl, R2 is isopropyl, R3 is linoleoyl (hereinafter, EC-A21).

The 1,2-diacylglycerol compound represented by Chemical formula 2 can be prepared using glycidyl chloride ($C_3H_5ClO$, molecular weight: 92.52) or Solketal (Solketal, $C_6H_{12}O_3$, molecular weight: 132.16) as a starting material. The synthesis method using glycidyl chloride as a starting material can be prepared by the following Reactions 1 to 3.

[Reaction 1]

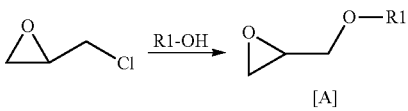

[A]

First, as shown in Reaction 1, glycidyl chloride and fatty acid (R1-OH, R1 is as defined in Chemical formula 2) are reacted to obtain compound A.

[Reaction 2]

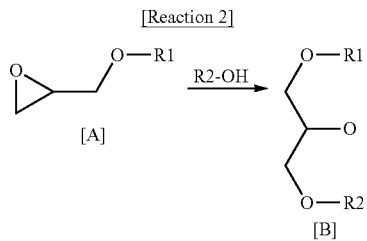

Next, as shown in Reaction 2, compound A and R2-OH (R2 is as defined in Chemical formula 2) are reacted to obtain compound B.

[Reaction 3]

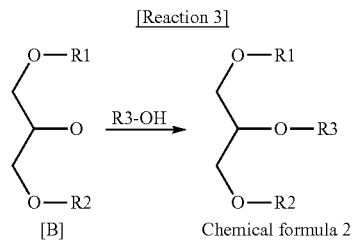

Next, as shown in Reaction 3, compound B and fatty acid (R3-OH, R3 is as defined in Chemical formula 2) are reacted to obtain a 1,2-diacylglycerol compound represented by Chemical formula 2.

Meanwhile, in the synthesis method using solketal as a starting material, first, reactions represented by the following Reaction 4 and 5 are performed to obtain compound B.

[Reaction 4]

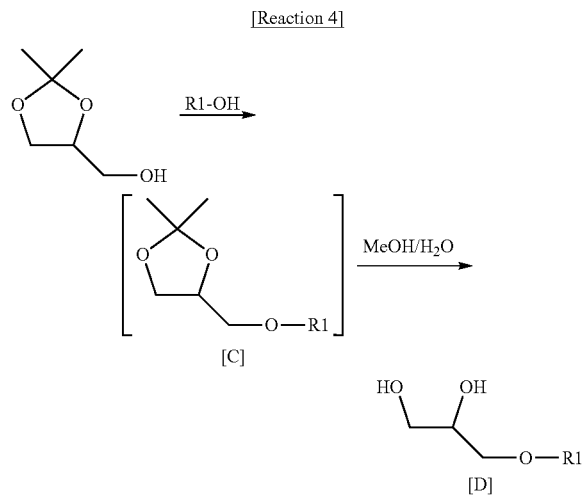

First, as shown in Reaction 4, solketal and fatty acid (R1-OH, R1 is as defined in Chemical formula 2) are reacted to obtain compound C. The compound C is subjected to a hydrolysis reaction to obtain compound D.

[Reaction 5]

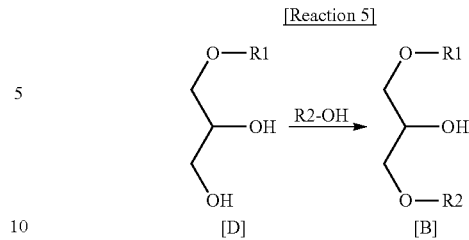

Next, as shown in Reaction 5, compound D and R2-OH (R2 is as defined in Chemical formula 2) are reacted to obtain compound B. Compound B thus obtained is used as a starting material. When the reaction of Reaction 3 is performed, a 1,2-diacylglycerol compound represented by Chemical formula 2 can be obtained.

The 1,2-diacylglycerol compound of the present invention, similar to the monoacetyldiacylglycerol derivative (EC-18) represented by Formula 1, which shows an effect in various acute and chronic inflammatory diseases as a conventional immunomodulator and anticancer agent, can regulate the expression of inflammatory cytokines in macrophages that initially respond to human infection, and can be used as an immunomodulator. Specifically, the 1,2-diacylglycerol compound of the present invention can inhibit overexpression of IL-6, an inflammatory cytokine, and reduce STAT3 activity, an IL-6 expression regulate factor. Therefore, it can be used as an improvement, prevention and therapeutic agent of various acute and chronic inflammatory diseases and diseases related to immune diseases. In addition, the 1,2-diacylglycerol compound of the present invention regulates and reduces the expression of IL-4 expressed in T hepler 2 type (Th2) T cells, which affects the microenvironment of various allergic and autoimmune diseases, and cancer. Also, since it has the effect of reducing the STAT6 activity, the expression regulate factor of these cytokines, it can be used as a preventive and therapeutic agent for Th2-related chronic diseases and cancer. Also, the 1,2-diacylglycerol compound of the present invention regulates and reduces the expression of CXCL8 (IL-8) in cells, and eventually reduces excessive neutrophil migration, and inhibits bacterial infection bronchial fungal infection of animal models. Therefore, as an immunomodulator that modulates inflammatory reaction by excessive neutrophil migration or as a therapeutic agent against initial infection, it can be usefully used as a prevention and therapeutic agent of various acute and chronic inflammatory diseases and diseases related to immune diseases. Therefore, the 1,2-diacylglycerol compound of the present invention inhibits overexpression of one or more inflammatory cytokines selected from the group consisting of IL-4, IL-6 and CXCL8 (IL-8), and may be usefully used for improving, preventing, or treating inflammation-related diseases. Examples of immune-related diseases that can be prevented or treated by the administration of the 1,2-diacylglycerol compound of the present invention may include various bacterial and viral infection diseases, acute and chronic inflammatory lung diseases, pneumonia, autoimmune disease, allergic disease, cancer, and so on. As used herein, the term "prevention" or "preventing" includes any activity to suppress the overexpression of immunity by administering the composition of the present invention. The term "treatment" or "treating" includes any activity to improve or beneficially alter the symptoms of immune-related diseases by the composition of the present invention.

1,2-diacylglycerol compound of present invention may be used as an immunomodulator alone without mixing other substance, or in the form of a pharmaceutical composition containing the 1,2-diacylglycerol compound as an active ingredient. When 1,2-diacylglycerol compound of present invention is used in the pharmaceutical composition, conventional pharmaceutically acceptable carriers, excipients, or diluents can be included therein. The amount of 1,2-diacylglycerol compound in the pharmaceutical composition can be widely varied without specific limitation, and is specifically 0.0001 to 100.0 weight %, specifically, 0.001 to 95.0 weight %. For example, the amount of the 1,2-diacylglycerol compound in the composition may be included in an amount of 0.01 to 50% by weight, more specifically 1 to 20% by weight. Also, the amount of the 1,2-diacylglycerol compound in the composition may be included in an amount of 50 to 100% by weight, more specifically 50 to 95% by weight.

The pharmaceutical composition may be formulated into any one selected from the group consisting of tablets, bolus, powders, granules, capsules, suspensions, liquid solutions, emulsions, syrups, sterilized aqueous solutions, non-aqueous solutions, suspensions, emulsions, freeze-dried agents, and suppositories and so on, and may be formulated into various forms for oral or non-oral administration. In formulating the composition, conventional excipients, or diluents such as fillers, bulking agents, binders, wetting agents, disintegrating agents, and surfactants can be used. The solid formulation for oral administration includes tablet, bolus, powder, granule, capsule and so on, and such solid formulations can be prepared by mixing one or more of the components and at least one excipient such as starch, calcium carbonate, sucrose, lactose, gelatin, and so on. Besides the excipient, a lubricant such as Magnesium stearate and talc can also be used. The liquid formulation for oral administration includes suspension, liquid solutions, emulsion, syrup, and so on, and may include conventional diluents such as water and liquid paraffin or may include various excipients such as wetting agents, sweeting agents, flavoring agents, and preserving agents. The formulation for non-oral administration includes sterilized aqueous solution, non-aqueous solution, suspension, emulsion, freeze-dried formulation, suppository, and so on, and solvent for solution such as non-aqueous solution, suspension may include propylene glycol, polyethylene glycol, vegetable oils such as olive oil, and ester for syringe injection such as ethyl oleate. Base materials of the suppository may include witepsol, macrogol, tween 61, cacao butter, Laurin and glycerogelatin.

The composition of present invention can be administered in a pharmaceutically effective amount. The term "pharmaceutically effective amount" is used to refer to an amount that is sufficient to treat a disease at a reasonable benefit/risk ratio applicable to achieve a desired result in a medical treatment. The "pharmaceutically effective amount" can be determined according to the subject's category, age, sex, severity and type of disease, activity of drug, sensitivity to drug, administration time, administration route, excretion rate, duration of treatment, factors including concurrent drugs, and other factors well known in the medical field. The composition of the present invention can be administered alone or with other therapeutic agents sequentially or simultaneously. The composition of the present invention can be administered once or multiple times. It is important to administer an amount capable of obtaining the maximum effect in a minimum amount without side effects in consideration of all of the above factors, which can be easily determined by a person skilled in the art. The preferable amount of the composition of the present invention can be varied according to the condition and weight of patient, severity of disease, formulation type of drug, administration route and period of treatment. An appropriate total amount of administration per 1 day can be determined by a physician, and is generally about 0.001 to about 1000 mg/kg, preferably about 0.05 to 200 mg/kg, more preferable about 0.1 to about 100 mg/kg once a day or can be administered in divided doses multiple times daily. The compound or composition can be applied to any subject without specific limitation as long as it is an individual for the purpose of preventing immunity reduction, of enhancing immunity, or of treating an immune disease. For example, the composition of the present invention can be administered to not only human but also non-human animal (specifically mammals) such as monkey, dog, cat, rabbit, guinea pig, rat, mouse, cow, sheep, pig, goat, and birds and fishes, and so on. The composition of the present invention can be administered by conventional various methods, for example, by oral or rectum administration, or by intravenous (i.v.), intramuscular (i.m.), subcutaneous (s.c.), intrauterine dural or cerebrovascular injection.

In some embodiments, the present invention provides health functional food compositions for regulating immunity, which comprises a 1,2-diacylglycerol compound of formula 1 as an active ingredient. Specifically, the 1,2-diacylglycerol compound of the present invention may be included in a health functional food composition for preventing immunity overexpression, enhancing immunity, preventing or improving immune-related diseases. The term "improvement" or "improving" refers to any activity to improve or ameliorate the symptoms of an individual who is suspicious of an immune-related disease or developing an immune-related disease.

The health functional food composition may consist of only or substantially pure compound of the present invention or may include compound of the present invention together with other conventional ingredients of health functional food. The amount of the active ingredient in the health food composition can be determined suitably according to the intended use. Generally, when the compound of the present invention is included in food or beverages, the amount of the composition according to the present invention is preferably less than 15 weight %, more preferably less than 10 weight %, with respect to the total amount of the raw material. In case of a long term use for the purpose of the health control and hygiene, the amount can be less than the above range. Since there is no problem in terms of safety, amount of the active component is greater than the above range.

Foods to which the compound of the present invention can be added are not limited, and include various foods, for example, meats, sausages, breads, chocolates, candies, snacks, pizzas, noodles, gums, daily products such as ice creams, soups, beverages, teas, drinks, alcoholic beverages, vitamin complexes and any health functional food, and also include food used as feed for animals. When the health functional food composition of present invention is used in the beverage product, the beverage product may include sweeting agents, flavoring agents or natural carbohydrates. Examples of natural carbohydrates include monosaccharides such as glucose and fructose, disaccharides such as maltose and sucrose, polysaccharides such as dextrin and cyclodextrin, and sugar alcohols such as xylitol, sorbitol and erythritol. The amount of carbohydrate in the beverage composition can be widely varied without specific limitation, and is preferably 0.01 to 0.04 g, more preferably, 0.02 to 0.03 g per 100 ml of the beverage. Examples of sweeting agents include natural sweeteners such as thaumatin and *stevia* extract and artificial sweeteners such as saccharin and aspartame. In addition to the above, the health functional food composition of the present invention may include various nutrients, vitamins, electrolytes, flavoring agents, colorants, pectic acid and salts thereof, alginic acid and salts thereof, organic acids, protective colloidal thickening agents, pH controlling agents, stabilizing agents, preserving agents, glycerin, alcohol, carbonizing agents used in carbonated beverages and so on. Moreover, the health functional food composition of the present invention may include fruits, as used in preparing natural fruit juices and fruit juice beverages and vegetable beverages.

In some embodiments, the present disclosure provides methods for regulating immunity or preventing or treating an immune overexpression or immune-related disease, comprising administering the pharmaceutical composition to a patient in need thereof. The term "a patient in need" includes any animal including human that suffers from immune-related disease or can develop immune-related disease. Immune overexpression or immune-related disease can be treated or prevented by administering an effective amount of a pharmaceutical composition containing a compound of the present invention or containing the compound of the present invention and pharmaceutically acceptable salt thereof to a patient in need thereof. The term "administration" means introducing the pharmaceutical composition of the present invention to a patient in need by any suitable method. The composition of the present disclosure can be administered by conventional various methods, for example, by oral or non-oral administration as far as the target organization can be reached. In some embodiments, the method of the present disclosure comprises administering a therapeutically effective amount of a pharmaceutical composition comprising 1,2-diacylglycerol compound of chemical formula 1 to a patient in need thereof. An appropriate total amount of administration per 1 day can be determined by a physician, and is generally about 0.001 to about 1000 mg/kg, preferably, about 0.05 to 200 mg/kg, more preferably about 0.1 to about 100 mg/kg. The total administration amount per day can be administered once a day or can be administered in divided doses multiple times daily. However, the specific therapeutically effective amount of pharmaceutical composition administered to a particular patient can be varied depending on the type and degree of the response to be achieved in the treatment, the specific composition, including whether another agent is included in the composition, the patient's age, body weight, general health status, sex, diet, administration time, administration route, the ratio of composition, treatment period, other drugs used together in the treatment and a variety of factors well known in the medical field.

EMBODIMENTS FOR CARRYING OUT THE INVENTION

Hereinafter, the present invention is described in more detail through examples. The following example is only to help the understanding of the present invention, and the present invention is not limited by the following examples.

[Example 1] Synthesis of 1,2-diacylglycerol Compound Using Glycidyl Chloride (EC-A14)

A. As shown in reaction 1a below, glycidyl chloride (832.68 mg, 9.0 mmol, 1.8eq.), R1-OH (1 eq., R1=palmitoyl), NaOH (1.8 eq.) and n-Bu$_4$NBr (0.05 eq.) as a catalyst were added to 1.5 ml of PE (petroleum ether) in a nitrogen atmosphere (N2-purge). And, the temperature was raised to 50° C. and it was stirred for 5 hours. The reaction solution was diluted with 30 ml of PE and then filtered. The organic layer was dehydrated with Na$_2$SO$_4$, and filtered, and then concentrated. The concentrate was purified with a flash column (PE:EA (ethyl acetate)=50:1) to obtain the target compound A (R1=palmitoyl, yield=63.65%).

[Reaction 1a]

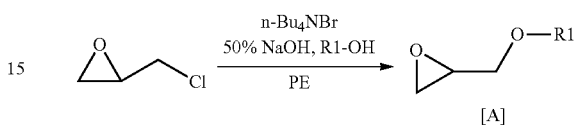

B. As shown in reaction 1b below, 200 mg (640 mmol, 1 eq.) of compound A obtained in the above step A, R2-OH (0.8eq. R2=ethyl), and n-Bu$_4$NBr (0.1 eq.) as a catalyst were added to 2 ml of ACN (acetonitrile). And the temperature was raised to 100° C. and it was stirred for 18 hours. The reaction solution was concentrated. The concentrate was purified with a flash column (PE:EA=20:1, Rf=0.18) to obtain the target compound B (R1=palmitoyl, R2=ethyl, yield=25.03%).

[Reaction 1b]

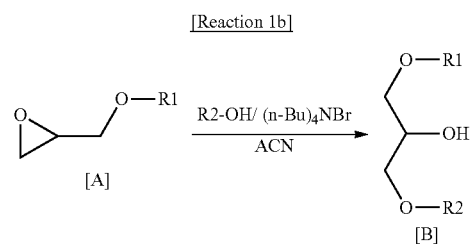

C. As shown in reaction 1c below, R3-OH (1.02eq., R3=linoleoyl), and pivaloyl chloride (1eq.) were added to 18 ml of hexane (Hex). And the temperature was cooled to 5° C. or less, and then triethylamine (TEA, 2eq.) was slowly added dropwise while maintaining at 10~15° C. Thereafter, it was stirred at the same temperature for 30 minutes. 2.284 g (6.37 mmole, 1 eq. R1=palmitoyl, R2=ethyl) of compound B obtained in step B and 4-dimethylaminopyridine (DMAP, 0.1eq.) were added, and it was maintained overnight while maintaining 20~25° C. (overnight). 0.16 ml of purified water was added and stirred for 2 hours. Then, 14 ml of purified water was added, and the layers were separated. Layer separation was performed twice with a solvent mixed with 9.13 ml of methanol (MeOH), 4.5 ml of purified water and 0.25 mg of KOH. Layer separation was performed twice with a solvent mixed with 13 ml of methanol (MeOH) and 0.7 ml of purified water. And then, layer separation was performed with a solvent in which 42 mg of c-HCl was mixed with 14 ml of purified water. 1.16 g of MgSO$_4$, 2.9 g of activated clay and 2.9 g of activated carbon were added to the organic layer. It was stirred at 10~15° C. for 1 hour and then filtered. It was washed with cooled hexane and concentrated. It was obtained the target compound (EC-A14, R1=palmitoyl, R2=ethyl, R3=linoleoyl) represented by Chemical formula 1 (yield: 22.03%).

[Reaction 1c]

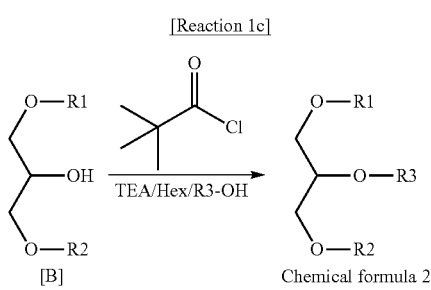

Chemical formula 2

[Example 2] Synthesis of 1,2-diacylglycerol Compound Using Solketal (EC-A78)

A. As shown in reaction 2a below, triethylamine (TEA, 2.09eq.) and R1-OH (1 eq., R1=palmitoyl) were dissolved in 33 ml of methylene chloride (MC). And, the reaction temperature was cooled to 5~15° C., and then pivaloyl chloride (1.05eq.) was added while maintaining 15° C. or less. It was stirred for 30 minutes. 2.54 ml (20.47 mmole, 1.05eq.) of solketal was quickly added to the reaction solution, and DMAP (0.01eq.) was added. Then, it was stirred at 20~25° C. for 1 hour. When the reaction was completed, 12.5 ml of purified water was added, and layer separation was performed. Again, 12.5 ml of purified water was added, and 0.3 ml of c-HCl was added to adjust the pH to 7~8. The organic layer was separated and then concentrated to obtain an oily compound. 15 ml of methanol (MeOH) and 1.75 ml of purified water were added thereto, and the temperature was set to 22~23° C. Then, 2 ml of c-HCl was slowly added dropwise. It was stirred for 2~2.5 hours while maintaining the temperature below 25° C. As a result, a white solid gradually was precipitated. 13 ml of hexane and 16 ml of purified water were added thereto, and 1.9 ml of pyridine was added while maintaining 25° C. After adjusting the pH to 4~5, and it was cooled to 15° C. and then filtered. It was washed with hexane and then dried. It was obtained the target compound D (R1=palmitoyl, yield: 85%).

[Reaction 2a]

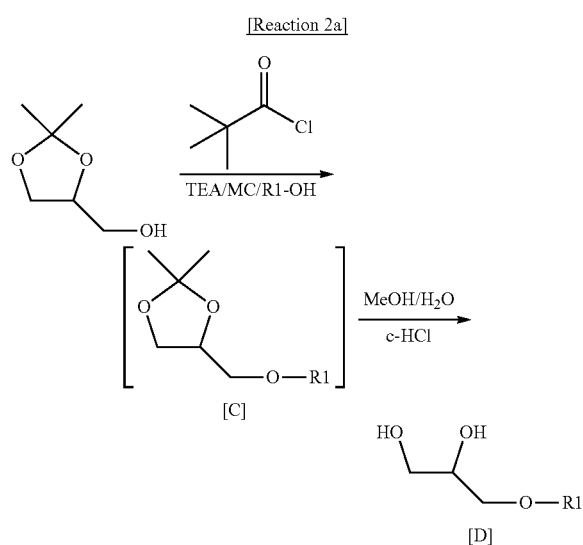

B. Next, as shown in reaction 2b below, 8.53 ml of pyridine, 5 g (R1=palmitoyl, 15.13 mmol, 1eq.) of compound D obtained in step A, and DMAP (0.02eq.) were added to 30 ml of methylene chloride (MC), and dissolved at 25~30° C. Then, the temperature was cooled to 20° C., and propionyl chloride (0.2eq) was slowly added dropwise. The reaction temperature was cooled to 18 to 19° C., and propionyl chloride (0.3eq) dissolved in methylene chloride was added dropwise. And the temperature was cooled to 13 to 15° C., and propionyl chloride (0.5eq) dissolved in methylene chloride was added dropwise. Again, the temperature was cooled to 5 to 10° C., and propionyl chloride (0.5eq) dissolved in methylene chloride was added dropwise, and stirred for 1 hour. At the same temperature, 20 ml of purified water was added, and 6 ml of c-HCl was added to adjust the pH to 1 to 2. The layer separation was performed, and the organic layer was neutralized with $K_2CO_3$ and $MgSO_4$, and concentrated by dehydration. In order to remove the remaining methylene chloride, it was concentrated with hexane. After adding 15 ml of hexane, the temperature was cooled to 18~20° C., and then crystals were precipitated by seeding. The reaction product was precipitated at a temperature of 13 to 15° C. Then, it was cooled to 10° C. again, and washed with cooled hexane, and then dried. It was obtained the target compound B (R1=palmitoyl, R2=propionyl, yield: 71.23%).

[Reaction 2b]

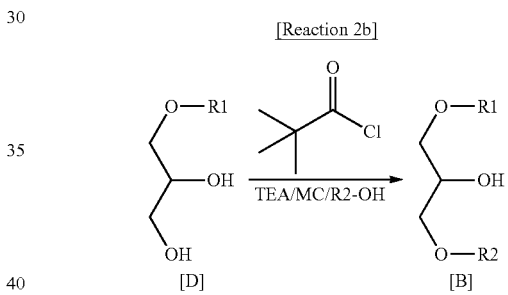

Using the thus obtained compound B (1 eq. R1=palmitoyl, R2=propionyl), according to reaction 1c of Example 1, the target compound (EC-A78, R1=palmitoyl, R2=propionyl, R3=linoleoyl) represented by Chemical formula 2 was obtained.

[Example 3] Synthesis of 1,2-diacylglycerol Compound (EC-A16)

A. As shown in reaction 3a below, 2.24 g (7.18 mmol, 1eq.) of target compound A of step A in Example 1, linoleic acid (1eq.) and n-$Bu_4NBr$ (0.1 eq.) as a catalyst were added to one portion to 10 ml of acetonitrile (ACN) in a nitrogen atmosphere (N2-purge). It was stirred, and heated to 100° C. and stirred for 16 hours. When the reaction was complete, it was cooled to 0° C., and 20 ml of $NH_4Cl$ solution was added to terminate the reaction. The aqueous layer was extracted three times with 125 ml of methylene chloride (MC), washed with brine solution, dehydrated with $Na_2SO_4$ and then concentrated. The concentrate was purified with a flash column (PE:EA=20:1) to obtain the target compound E (R1=palmitoyl, R3=linoleoyl, yield: 5.58%).

[Reaction 3a]

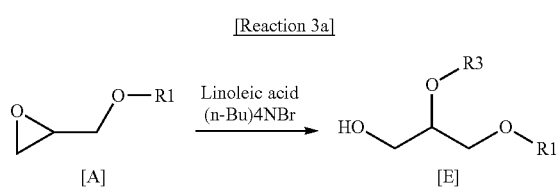

B. As shown in reaction 3b below, 60 mg (101.19 μmole, 1eq.) of target compound E of the step A, linoleic acid (1eq.), benzoic acid (1.2eq.), N,N'-dicyclohexylcarbodiimide (DCC, 1.2eq.) and DMAP (0.1eq.) were added to 3 ml of methylene chloride at 0° C. in a nitrogen atmosphere (N$_2$-purge). It was stirred for 15 minutes. The reaction solution was heated to 20° C. and stirred for 48 hours. When the reaction was complete, it was filtered and extracted three times with purified water and brine solution. The extracted organic layer was dehydrated with Na$_2$SO$_4$ and concentrated. The concentrate was purified with a flash column (PE:EA=10:1) to obtain the target compound F (EC-A16, R1=palmitoyl, R3=linoleoyl, R2=benzoyl, yield: 26.94%).

[Reaction 3b]

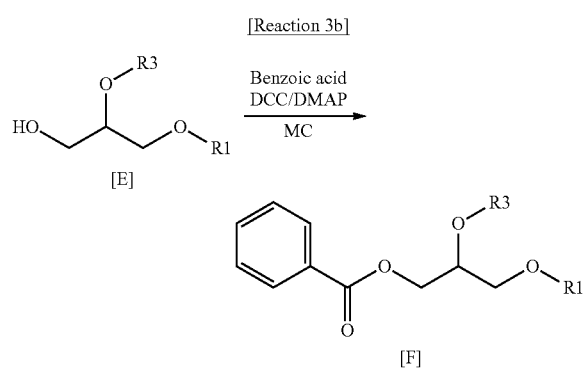

[Example 4] Synthesis of 1,2-diacylglycerol Compound (EC-A57)

A. As shown in reaction 4a below, 800 mg (1.35 mmole, 1 eq.) of target compound E of step B in Example 3, N-(tert-butoxycarbonyl)glycine (Boc-glycine, 1.2eq.), N,N'-dicyclohexylcarbodiimide (DCC, 1.2eq.) and DMAP (0.2eq.) were added to 4 ml of methylene chloride at 25° C. in a nitrogen atmosphere (N$_2$-purge). It was stirred for 18 hours. When the reaction was complete, it was filtered, and extracted three times with purified water and brine solution. The extracted organic layer was dehydrated with Na$_2$SO$_4$ and concentrated. The concentrate was purified with a flash column (PE:EA=50:1) to obtain the target compound G (R1=palmitoyl, R3=linoleoyl, yield: 46.91%).

[Reaction 4a]

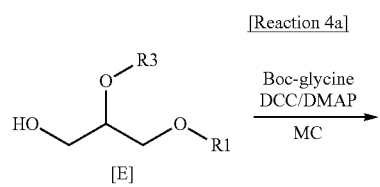

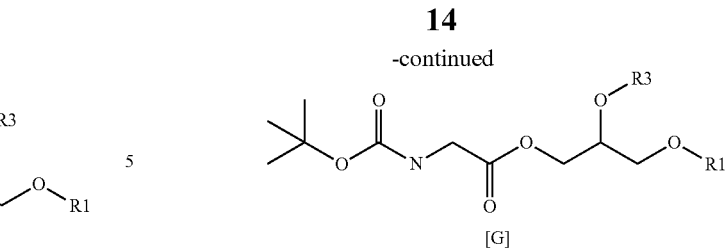

B. As shown in reaction 4b below, 100 mg (133.32 μmole, 1eq.) of target compound G of step A, linoleic acid (1eq.) and trifluoroacetic acid (TFA, 20eq.) were added to 1 ml of methylene chloride at 0° C. in a nitrogen atmosphere (N$_2$-purge). It was stirred for 10 minutes. When the reaction was complete, the reaction solution was concentrated. The concentrate was purified with a flash column (PE:EA=50:1) to obtain the target compound H (EC-A57, yield: 52.51%).

[Reaction 4b]

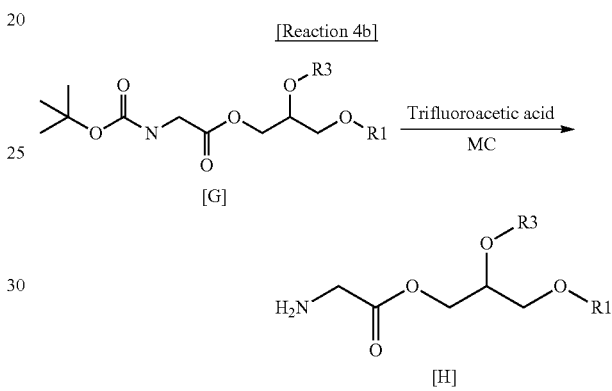

[Example 5] Synthesis of 1,2-diacylglycerol Compound (EC-A70-1)

A. As shown in reaction 5a below, 50 mg (554.82 μmole, 1eq.) of 1,1-dimethoxyethane, 2,4,6-trimethylpyridine(2,4,6-collidine, 3eq.) and trimethylsilyl trifluoromethane sulfonate (TMSOTf, 2eq.) were added to 5 ml of methylene chloride at 0° C. in a nitrogen atmosphere (N$_2$-purge). It was stirred for 2 hours. It was obtained to the target compound I. The obtained reaction solution was immediately used for the next reaction without work-up and purification.

[Reaction 5a]

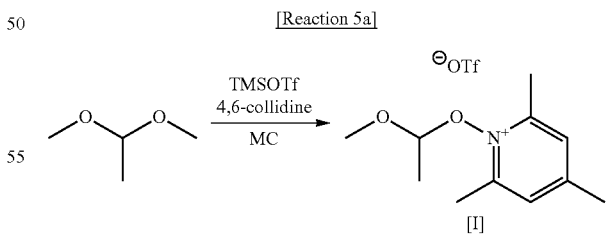

B. As shown in reaction 5b below, 250 mg (421.63 μmole, 1 eq.) of target compound E of step A in the Example 3 was added to the reaction solution of the step A in a nitrogen atmosphere (N$_2$-purge). It was stirred at 28° C. for 20 hours. When the reaction was complete, the reaction was terminated by adding 20 ml of purified water. It was extracted twice with 20 ml of methylene chloride. The extracted organic layer was dehydrated with Na$_2$SO$_4$ and concentrated. The concentrate was purified with a flash column (PE:EA=10:1) to obtain the target compound J (EC-A70-1, R1=palmitoyl, R3=linoleoyl, yield: 20.77%).

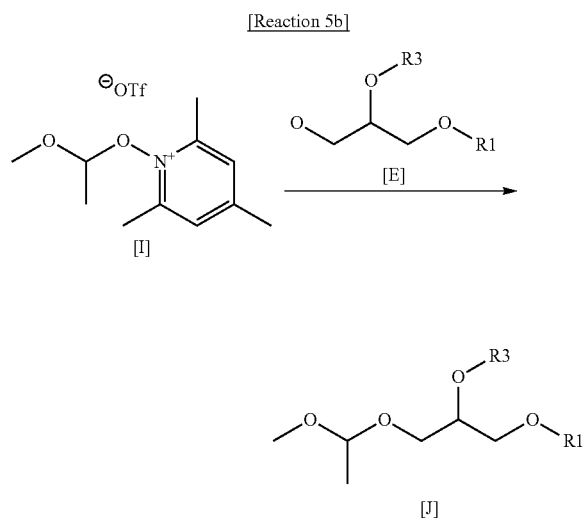

[Reaction 5b]

[Example 6 to 33] Synthesis of 1,2-diacylglycerol Compound

In substance the same method as in Examples 1 to 5, 1,2-diacylglycerol compounds shown in Table 1 below were synthesized. It was shown in Table 1 together with the yield of the final synthesis step.

[Experimental Example 1] LPS-Induced IL-6 Secretion Reduction

In DMEM (Dulbecco Modified Eagle Medium, Hyclone, Thermo Scientific) medium to which 10% Fetal Bovine Serum was added, RAW264.7 cells, a mouse macrophage family, were suspended at a concentration of $1 \times 10^5$ cells/ml, and culture was conducted in a 5% $CO_2$ humidified incubator at 37° C. The cultured RAW264.7 cells were inoculated into a 48 well plate by $5 \times 10^4$ cells/ml and stabilized for 15 hours. Then, the culture solution was treated with a glycerol derivative compounds of the type shown in Table 2 and 3 below for 1 hour and then was treated with 1 μg/ml of Lipopolysaccharide (LPS) of a cell stimulator, and subsequent further incubation was conducted for 24 hours. Thereafter 0.5 ml of the culture supernatant was collected for each well and centrifuged (at 3000 rpm, 5 minutes) to recover the supernatant. The IL-6 level in the recovered supernatant was measured according to the manual provided by the Mouse IL-6 ELISA set (BD Biosciences). The day before ELISA was carried out, the IL-6 capture antibody was diluted in phosphate buffered saline, coated on a microwell, and then stored at 4° C. overnight. Each well was washed three times with a buffer solution and then blocked with 2% Bovine Serum Albumin (BSA) for 1 hour at room temperature. After washing with buffer solution three times, 1000 of sample was dispensed into each well and left at room temperature for 2 hours. Detection antibody which was washed 3 times with washing buffer solution and diluted was dispensed into each well and allowed to react at room temperature for 1 hour and left at room temperature for 1 hour. Thereafter, the secondary HRP conjugated antibody was reacted at room temperature for 30 minutes, washed three times with a buffer

TABLE 1

| Example No. | Compound | R1 group | R2 group | R3 group | Yield(%) |
|---|---|---|---|---|---|
| 1 | EC-A14 | Palmitoyl | Ethyl | Linoleoyl | 22.03 |
| 2 | EC-A78 | Palmitoyl | Propionyl | Linoleoyl | 71.23 |
| 3 | EC-A16 | Palmitoyl | Benzoyl | Linoleoyl | 26.94 |
| 4 | EC-A57 | Palmitoyl | 2-Aminoacetyl | Linoleoyl | 52.51 |
| 5 | EC-A70-1 | Palmitoyl | 1-Methoxyethyl | Linoleoyl | 20.77 |
| 6 | EC-A13 | Palmitoyl | Methyl | Linoleoyl | 10.98 |
| 7 | EC-A15 | Palmitoyl | Propyl | Linoleoyl | 15.76 |
| 8 | EC-A17 | Palmitoyl | Butyryl | Linoleoyl | 24.07 |
| 9 | EC-A18 | Palmitoyl | Valeroyl | Linoleoyl | 68.97 |
| 10 | EC-A19 | Palmitoyl | Isobytyryl | Linoleoyl | 39.86 |
| 11 | EC-A20 | Palmitoyl | 2-Methylbutyryl | Linoleoyl | 62.58 |
| 12 | EC-A21 | Palmitoyl | Isopropyl | Linoleoyl | 16.32 |
| 13 | EC-A22 | Palmitoyl | Pivaloyl | Linoleoyl | 69.96 |
| 14 | EC-A79 | Palmitoyl | Cyclopropanecarbonyl | Linoleoyl | 25.13 |
| 15 | EC-A83 | Palmitoyl | Enanthic | Linoleoyl | 43.06 |
| 16 | EC-A84 | Palmitoyl | Pelargonyl | Linoleoyl | 30.89 |
| 17 | EC-A85 | Octanoyl | Butyryl | Linoleoyl | 69.64 |
| 18 | EC-A86 | Octanoyl | Valeroyl | Linoleoyl | 54.92 |
| 19 | EC-A87 | Octanoyl | Propionyl | Linoleoyl | 53.30 |
| 20 | EC-A88 | Octanoyl | Isobytyryl | Linoleoyl | 39.37 |
| 21 | EC-A89 | Octanoyl | Pivaloyl | Linoleoyl | 54.35 |
| 22 | EC-A91 | Lauroyl | Propionyl | Linoleoyl | 51.04 |
| 23 | EC-A92 | Lauroyl | Butyryl | Linoleoyl | 39.33 |
| 24 | EC-A93 | Lauroyl | Valeroyl | Linoleoyl | 59.19 |
| 25 | EC-A94 | Lauroyl | Isobytyryl | Linoleoyl | 61.10 |
| 26 | EC-A95 | Lauroyl | Pivaloyl | Linoleoyl | 53.58 |
| 27 | EC-A96 | Lauroyl | 2-Methylbutyryl | Linoleoyl | 63.86 |
| 28 | EC-A97 | Decanoyl | Propionyl | Linoleoyl | 52.10 |
| 29 | EC-A98 | Decanoyl | Butyryl | Linoleoyl | 41.27 |
| 30 | EC-A99 | Decanoyl | Valeroyl | Linoleoyl | 49.25 |
| 31 | EC-A100 | Decanoyl | Isobytyryl | Linoleoyl | 63.79 |
| 32 | EC-A101 | Decanoyl | Pivaloyl | Linoleoyl | 58.21 |
| 33 | EC-A102 | Decanoyl | 2-Methylbutyryl | Linoleoyl | 64.92 | solution, and treated with 50 µl of stop solution for each well, and then the optical density was measured at 450 nm with an ELISA microplate leader. The results of the IL-6 expression reduction rate (IL-6 concentration) are shown in Table 2, Table 3, FIG. 1 and FIG. 2 below.

TABLE 2

| Experiment | Sample | Concentration (µg/ml) | IL-6 concentration (µg/ml, average ± deviation) |
|---|---|---|---|
| 1 | Negative control group | 0 | 0.045 ± 0.001 |
| 2 | DMSO | 0 | 0.045 ± 0.004 |
| 3 | LPS | 1 | 0.262 ± 0.008 |
| 4 | EC-18 | 100 | 0.194 ± 0.011 |
| 5 | EC__A13 | 100 | 0.266 ± 0.024 |
| 6 | EC__A14 | 100 | 0.277 ± 0.002 |
| 7 | EC__A15 | 100 | 0.125 ± 0.003 |
| 8 | EC__A16 | 100 | 0.238 ± 0.008 |
| 9 | EC__A17 | 100 | 0.154 ± 0.001 |
| 10 | EC__A18 | 100 | 0.147 ± 0.003 |
| 11 | EC__A19 | 100 | 0.204 ± 0.014 |
| 12 | EC__A20 | 100 | 0.055 ± 0.001 |
| 13 | EC__A21 | 100 | 0.176 ± 0.002 |
| 14 | EC__A22 | 100 | 0.174 ± 0.011 |
| 15 | EC__A57 | 100 | 0.120 ± 0.002 |
| 16 | EC__A70-1 | 100 | 0.144 ± 0.028 |

TABLE 3

| Experiment | Sample | Concentration (µg/ml) | IL-6 concentration (pg/µl, average ± deviation) |
|---|---|---|---|
| 1 | Negative control group | 0 | 0.073 ± 0.001 |
| 2 | DMSO | 0 | 0.071 ± 0.000 |
| 3 | LPS | 1 | 0.738 ± 0.057 |
| 4 | EC-18 | 100 | 0.491 ± 0.063 |
| 5 | EC__A78 | 100 | 0.708 ± 0.086 |
| 6 | EC__A79 | 100 | 0.652 ± 0.145 |
| 7 | EC__A83 | 100 | 0.658 ± 0.070 |
| 8 | EC__A84 | 100 | 0.799 ± 0.025 |
| 9 | EC__A85 | 100 | 0.741 ± 0.071 |
| 10 | EC__A86 | 100 | 0.796 ± 0.045 |
| 11 | EC__A87 | 100 | 0.705 ± 0.158 |
| 12 | EC__A88 | 100 | 0.792 ± 0.086 |
| 13 | EC__A89 | 100 | 0.736 ± 0.097 |
| 14 | EC__A91 | 100 | 0.752 ± 0.068 |
| 15 | EC__A92 | 100 | 0.800 ± 0.038 |
| 16 | EC__A93 | 100 | 0.765 ± 0.055 |
| 17 | EC__A94 | 100 | 0.702 ± 0.079 |
| 18 | EC__A95 | 100 | 0.777 ± 0.020 |
| 19 | EC__A96 | 100 | 0.788 ± 0.006 |
| 20 | EC__A97 | 100 | 0.745 ± 0.015 |
| 21 | EC__A98 | 100 | 0.619 ± 0.036 |
| 22 | EC__A99 | 100 | 0.666 ± 0.075 |
| 23 | EC__A100 | 100 | 0.749 ± 0.054 |
| 24 | EC__A101 | 100 | 0.645 ± 0.057 |
| 25 | EC__A102 | 100 | 0.738 ± 0.070 |

Figure 2:
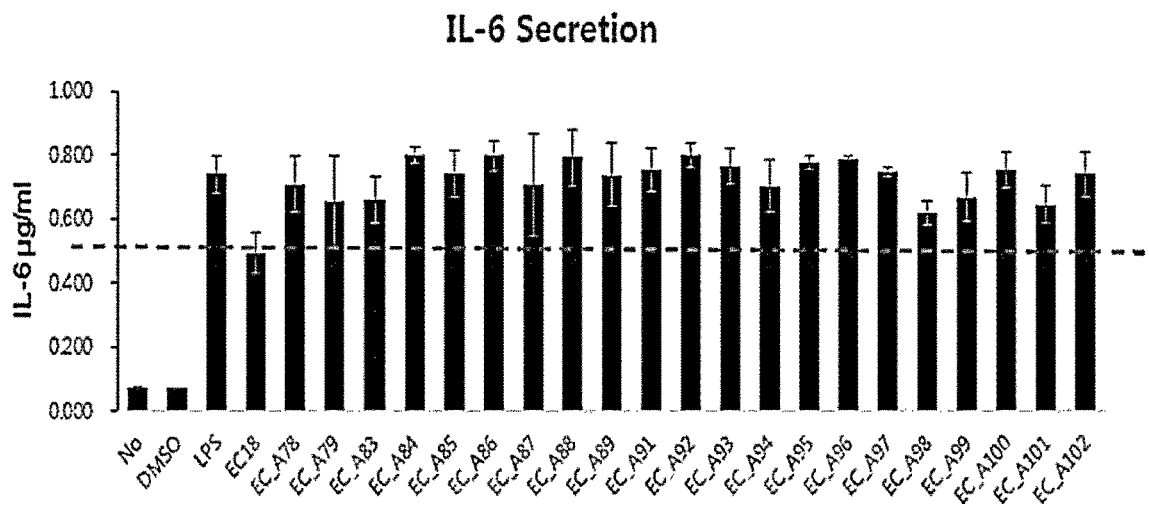

As shown in Table 2, Table 3, FIG. 1 and FIG. 2, it was confirmed that when RAW264.7 cells were treated with LPS, an inflammation-induced factor, the secretion of IL-6, an inflammatory cytokines, was increased by about six to ten times compared to the negative control group (Experiment number 3). When EC-18 (1-palmitoyl-2-linoleoyl-3-acetylglycerol, PLAG) compound, a substance that inhibits the expression of inflammatory cytokines, was added, IL-6 expression was decreased about 30% compared to the LPS-treated group (Experiment number 4). Meanwhile, among the compounds of the present invention, the compounds of A15, A17, A18, A19, A20, A21, A22, A57, A70-1 were decreased the secretion of IL-6 cytokines by 30% to 80% in RAW264.7 cells, so that it were inhibited IL-6 expression similar to or superior to EC-18 (PLAG).

[Experimental Example 2] IL-6-Induced STAT3 Activity Reduction

HEK-Blue™ IL-6 cells were used to confirm STAT3 activity by STAT3-induced SEAP (secreted embryonic alkaline phosphatase) expression. In DMEM (Hyclone, Thermo Scientific) medium to which 10% Fetal Bovine Serum was added, HEK-Blue™ IL-6 cells were cultured at a concentration of $1\times10^5$ cells/ml, and maintained in a 5% $CO_2$ humidified incubator at 37° C. The cultured HEK-Blue™ IL-6 cells were inoculated by $1\times10^5$ cells/ml. Then, the culture solution was treated with a glycerol derivative compounds of the type shown in Table 4 below for 1 hour and then IL-6 (5 ng/ml) was further incubated for 24 hours for STAT3 activity. Thereafter, the culture supernatant was collected for each well and centrifuged (at 3000 rpm, 5 minutes) to recover the supernatant. The SEAP expression level in the recovered supernatant was mixed with Quanti blue reagent and the supernatant at a ratio of 1:10 and left at 37° C. for about 30 minutes. Then, the SEAP concentration was confirmed at 650 nm wavelength using a spectrophotometer, and the results (STAT3 activity inhibitory ability) thereof are shown in Table 4 and FIG. 3 below.

TABLE 4

| Experiment | Sample | Concentration (µg/ml) | STAT3 activity__SEAP expression(%) (average ± deviation) |
|---|---|---|---|
| 1 | Negative control group | 0 | 100 |
| 2 | IL-6 | 5 ng/ml | 228.8 ± 17.0 |
| 3 | EC__18 | 100 | 173.0 ± 7.9 |
| 4 | EC__A13 | 100 | 167.2 ± 8.4 |
| 5 | EC__A14 | 100 | 185.0 ± 30.0 |
| 6 | EC__A15 | 100 | 232.0 ± 50.4 |
| 7 | EC__A16 | 100 | 171.1 ± 17.5 |
| 8 | EC__A17 | 100 | 185.4 ± 19.3 |
| 9 | EC__A18 | 100 | 166.2 ± 29.6 |
| 10 | EC__A19 | 100 | 162.9 ± 33.2 |
| 11 | EC__A20 | 100 | 196.7 ± 35.1 |
| 12 | EC__A21 | 100 | 224.1 ± 22.4 |
| 13 | EC__A22 | 100 | 169.5 ± 10.5 |
| 14 | EC__A57 | 100 | 243.0 ± 29.5 |
| 15 | EC__A70-1 | 100 | 259.5 ± 28.4 |

Figure 3:
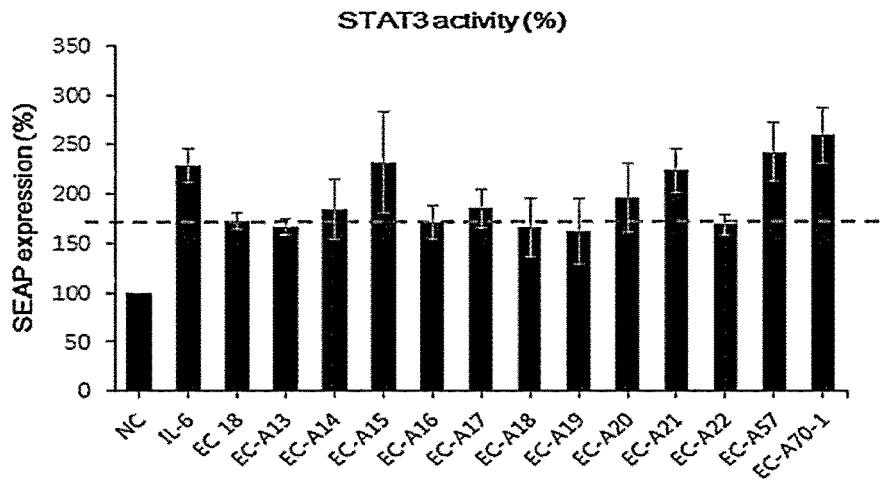
FIGS. 3 and 4 are graphs showing the effect of STAT3 activity reduction of the conventional and diacylglycerol derivative compound according to the present invention.

As shown in Table 4 and FIG. 3, it was confirmed that when IL-6 cytokine was treated in HEK-Blue™ IL-6 cells, the STAT3 activity was increased by about 2.3 times compared to the negative control group (Experiment 2). The EC-18 (PLAG)-treated group decreased STAT3 activity by about 25% compared to the IL-6 cytokine-treated group (Experiment 3). Meanwhile, among the compounds of the present invention, the compounds of A13, A16, A17, A18, A18, A22 were decrease the STAT3 activity by about 25%, so that it were inhibited STAT3 activity similar to or superior to EC-18 (FLAG).

[Experimental Example 3] IL-6-Induced STAT3 Activity Reduction pGL4.47 [luc2P/SIE/Hygro] vector containing the sis-Inducible Element that binds to STAT3 was injected into RAW264.7 cells to confirm the degree of STAT3 activity. In DMEM (Hyclone, Thermo Scientific) medium to which 10% Fetal Bovine Serum was added, RAW264.7 cells were cultured at a concentration of $1\times10^5$ cells/ml, and maintained in a 5% $CO_2$ humidified incubator at 37° C. The cultured RAW264.7 cells were inoculated into a 48 well plate by $1\times10^5$ cells/ml and stabilized for 18 hours. Thereafter, the pGL4.47 [luc2P/SIE/Hygro] vector containing sis-Inducible Element was mixed with Attractene to induce complex formation at room temperature for 15 minutes. This complex was treated with the cells and then further incubated for 18 hours. Thereafter, the culture solution was treated with a glycerol derivative compounds of the type shown in Table 5 below for 1 hour and then LPS (1 μg/ml) was treated and further incubated for 18 hours for STAT3 activity. Thereafter, the culture supernatant was removed for each well, and the remaining cells were lysed with a cell lysis buffer, and then cell lysate was recovered. 90 μl of luciferase reagent was mixed with 10 μl of the recovered cell lysate, and the degree of fluorescence was confirmed using a luminometer. The results are shown in Table 5 and FIG. 4 below.

TABLE 5

|   | Sample | Concentration (μg/ml) | STAT3 activity_Luciferase activity (average ± deviation) |
|---|---|---|---|
| 1 | Negative control group | 0 | 405.7 ± 81.6 |
| 2 | DMSO |  | 372.7 ± 25.1 |
| 3 | LPS | 1 | 879 ± 292.7 |
| 4 | EC-18 | 100 | 491.5 ± 41.7 |
| 5 | EC_A78 | 100 | 912.5 ± 214.2 |
| 6 | EC_A79 | 100 | 1183.5 ± 51.6 |
| 7 | EC_A83 | 100 | 510.2 ± 27.2 |
| 8 | EC_A84 | 100 | 780 ± 27.5 |
| 9 | EC_A85 | 100 | 1126.7 ± 32.1 |
| 10 | EC_A86 | 100 | 866.2 ± 15.2 |
| 11 | EC_A87 | 100 | 1312 ± 34.6 |
| 12 | EC_A88 | 100 | 1171.5 ± 146.3 |
| 13 | EC_A89 | 100 | 1087.7 ± 257.7 |
| 14 | EC_A91 | 100 | 746.5 ± 26.1 |
| 15 | EC_A92 | 100 | 820 ± 448.3 |
| 16 | EC_A93 | 100 | 536.2 ± 222.3 |
| 17 | EC_A94 | 100 | 640 ± 275.7 |
| 18 | EC_A95 | 100 | 663 ± 61.5 |
| 19 | EC_A96 | 100 | 1136.7 ± 63.9 |
| 20 | EC_A97 | 100 | 573.2 ± 146.7 |
| 21 | EC_A98 | 100 | 370.7 ± 35.0 |
| 22 | EC_A99 | 100 | 353.2 ± 83.0 |
| 23 | EC_A100 | 100 | 572.2 ± 60.4 |
| 24 | EC_A101 | 100 | 581.7 ± 8.1 |
| 25 | EC_A102 | 100 | 602 ± 11.3 |

Figure 4:
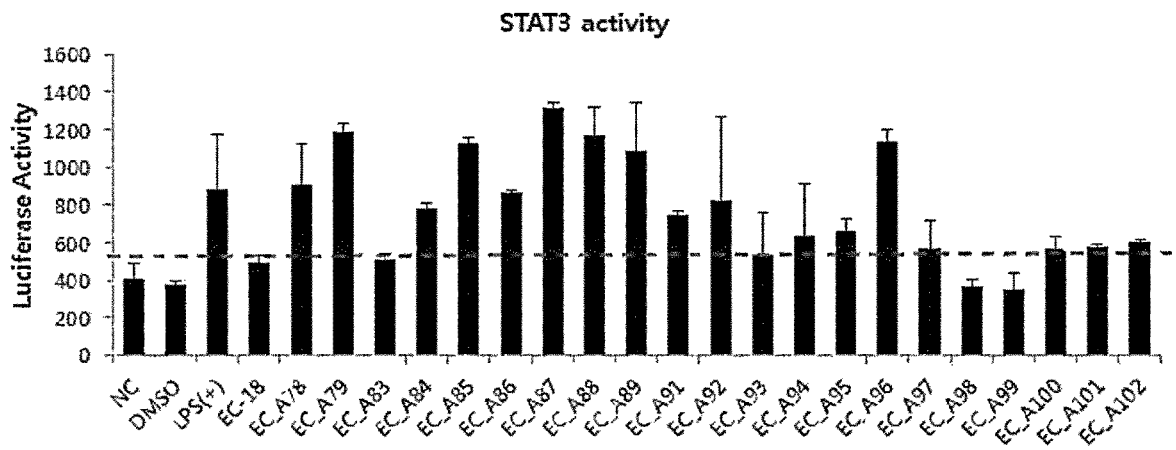

As shown in Table 5 and FIG. 4, it was confirmed that when LPS was treated in RAW264.7 cells, the STAT3 activity was increased by about 2.2 times compared to the negative control group (Experiment 3). The EC-18 (PLAG)-treated group decreased STAT3 activity to a degree similar to that of the negative control group. Meanwhile, among the glycerol derivative compounds of the present invention, most of the compounds of A83, A93, A97, A98, A99, A100, A101, A102 were confirmed to have decreased the STAT3 activity similar to the negative control and EC-18 (FLAG).

[Experimental Example 4] CXCL8 (IL-8) Expression Reduction in THP-1 Cells

In RPMI (Hyclone, Thermo Scientific) medium to which 10% Fetal Bovine Serum was added, THP-1 cells, a human macrophage family, were suspended at a concentration of $1\times10^5$ cells/ml, and culture was conducted in a 5% $CO_2$ humidified incubator at 37° C. The cultured THP-1 cells were inoculated into a 12 well plate by $1\times10^6$ cells/ml and stabilized for 30 minutes. Then, the culture solution was treated with a glycerol derivative compounds of the type shown in Table 6 below for 1 hour and then was treated with Gemcitabine (2 μg/ml) of a cell stimulator, and subsequent further incubation was conducted for 24 hours. Thereafter 1.5 ml of the culture supernatant was collected for each well and centrifuged (at 3000 rpm, 5 minutes) to recover the supernatant. The CXCL8 (IL-8) level in the recovered supernatant was measured according to the manual provided by the human IL-8 ELISA set (BD Biosciences). The day before ELISA was carried out, the IL-8 capture antibody was diluted in phosphate buffered saline, coated on a microwell, and then stored at 4° C. overnight. Each well was washed three times with a buffer solution and then blocked with 2% Bovine Serum Albumin (BSA) for 1 hour at room temperature. After washing with washing buffer solution three times, 100 μl of sample was dispensed into each well and left at room temperature for 2 hours. Detection antibody which was washed 3 times with washing buffer and diluted was dispensed into each well and allowed to react at room temperature for 1 hour and left at room temperature for 1 hour. Thereafter, the secondary HRP conjugated antibody was reacted at room temperature for 30 minutes, washed three times with a washing buffer, and treated with 50 μl of stop solution for each well, and then the optical density was measured at 450 nm with an ELISA microplate leader. The results of the measured CXCL8 (IL-8) expression increase rate were shown in Table 6 and FIG. 5 below.

TABLE 6

| Example | Sample | Concentration (μg/ml) | CXCL8 [IL-8] concentration (pg/μl, average ± deviation) |
|---|---|---|---|
| 1 | Negative control group | 0 | 7.9 ± 0.0 |
| 2 | Gemcitabine | 2 | 104.6 ± 1.5 |
| 3 | EC_18 | 100 | 79.6 ± 6.0 |
| 4 | EC_A13 | 100 | 96.6 ± 0.2 |
| 5 | EC_A15 | 100 | 73.8 ± 0.0 |
| 6 | EC_A16 | 100 | 135.1 ± 2.3 |
| 7 | EC_A17 | 100 | 110 ± 0.2 |
| 8 | EC_A18 | 100 | 84.0 ± 1.8 |
| 9 | EC_A19 | 100 | 277.9 ± 3.1 |
| 10 | EC_A21 | 100 | 86.2 ± 0.7 |
| 11 | EC_A22 | 100 | 105.3 ± 3.6 |
| 12 | EC_A43 | 100 | 100.7 ± 0.7 |
| 13 | EC_A70-1 | 100 | 200.1 ± 1.0 |
| 14 | EC_A78 | 100 | 108.5 ± 4.9 |
| 15 | EC_A79 | 100 | 108.7 ± 8.3 |
| 16 | EC_A83 | 100 | 107.7 ± 3.9 |
| 17 | EC_A84 | 100 | 110.5 ± 6.8 |
| 18 | EC_A85 | 100 | 94.4 ± 3.4 |
| 19 | EC_A86 | 100 | 99.2 ± 4.9 |
| 20 | EC_A87 | 100 | 134.4 ± 10.7 |
| 21 | EC_A88 | 100 | 91.4 ± 3.4 |
| 22 | EC_A89 | 100 | 123.1 ± 0.0 |
| 23 | EC_A91 | 100 | 96.1 ± 3.6 |
| 24 | EC_A92 | 100 | 105.1 ± 0.2 |
| 25 | EC_A93 | 100 | 110.9 ± 0.0 |
| 26 | EC_A96 | 100 | 103.7 ± 5.4 |
| 27 | EC_A97 | 100 | 96.2 ± 0.2 |
| 28 | EC_A98 | 100 | 105 ± 2.0 |
| 29 | EC_A99 | 100 | 102.0 ± 19.3 |
| 30 | EC_A100 | 100 | 115.1 ± 3.9 |
| 31 | EC_A101 | 100 | 118.1 ± 2.8 |
| 32 | EC_A102 | 100 | 102.5 ± 4.4 |

Figure 5:
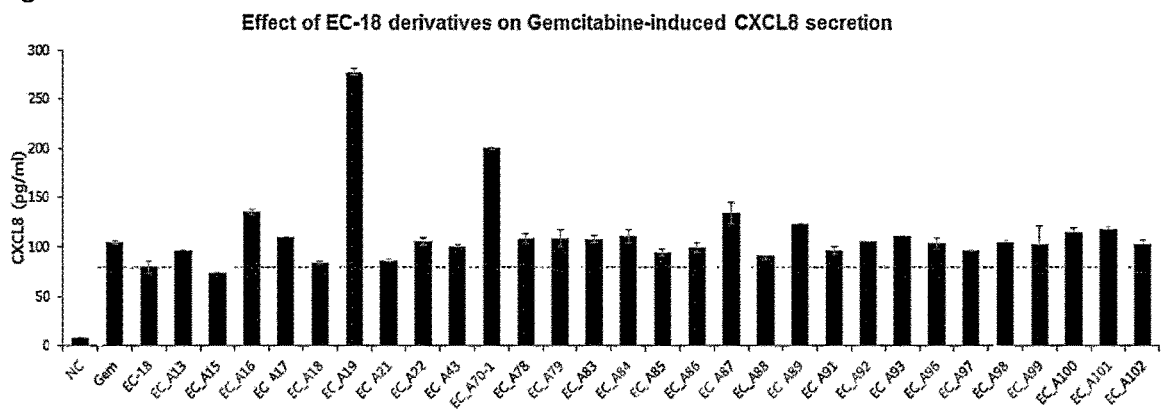
FIG. 5 is a graph showing the effect of CXCL8 (IL-8) expression reduction of the conventional and diacylglycerol derivative compound according to the present invention.

As shown in Table 6 and FIG. 5, it was confirmed that when Gemcitabine, an anticancer drug, was treated in THP-1 cells, the secretion of CXCL8 (IL-8) chemokine, a neutrophil cell recruitment factor, was increased by about 13 times compared to the negative control group (Experiment 2). When the EC-18 (PLAG) was treated, it was reduced CXCL8 expression by about 20% (Experiment 3). Meanwhile, among the glycerol derivative compounds of the present invention, the compounds of A15, A18, A21 were decreased the secretion of CXCL8 (IL-8) chemokine by about 20% similar to the EC-18 (PLAG).

[Experimental Example 5] Reduction in Migration of HL-60 Cell Line

In RPMI (Hyclone, Thermo Scientific) medium to which 10% Fetal Bovine Serum was added, THP-1 cells, a human macrophage family, were subcultured at a concentration of $1\times10^5$ cells/ml, and culture was conducted in a 5% $CO_2$ humidified incubator at 37° C. In order to prepare the THP-1 cell culture solution to be treated in the lower well during the transmigration assay, first, the cultured THP-1 cells were inoculated into a 12 well plate by $1\times10^6$ cells/ml and stabilized for 30 minutes. Then, the culture solution was treated with a glycerol derivative compounds of the type shown in Table 7 below for 1 hour and then was treated with Gemcitabine (2 μg/ml) of a cell stimulator, and subsequent further incubation was conducted for 24 hours. Thereafter 1.5 ml of the culture supernatant was collected for each well and centrifuged (at 3000 rpm, 5 minutes) to recover the supernatant. The CXCL8 (IL-8) level in the recovered supernatant was measured according to the manual provided by Cultrex 96 well Laminin Cell Invasion assay. The day before Transmigration assay was carried out, a 1× Lamin I solution was treated in the upper Invasion Chamber and coated. Thereafter, in RPMI (Hyclone, Thermo Scientific) medium to which 10% Fetal Bovine Serum was added, the cultured HL-60 cells were despensed of $5\times10^4$ cells/chamber, and 150 μl of the THP-1 culture supernatant prepared in advance was added to the lower chamber. Thereafter the upper chamber was removed, and the cells were attached to the bottom of the lower chamber by a centrifuge, and then the supernatant was removed. Cell dissociation/Calcein-AM solution was added and reacted for 1 hour. Then, the value obtained using a fluorescence spectroscopy was calculated by converting the number of cells. The results of the reduction in migration of HL-60 cells were shown in Table 7 and FIG. 6 below.

TABLE 7

| Example | Sample | Concentration (μg/ml) | Number of HL-60 cells migrated through Transwell (Cell Number) |
|---|---|---|---|
| 1 | Negative control group | 0 | 2582.6 |
| 2 | Gemcitabine | 2 | 5022.9 |
| 3 | EC_18 | 100 | 2697.2 |
| 4 | EC_A13 | 100 | 8679.7 |
| 5 | EC_A15 | 100 | 28884.8 |
| 6 | EC_A16 | 100 | 26348.9 |
| 7 | EC_A17 | 100 | 30692.8 |
| 8 | EC_A18 | 100 | 9891.6 |
| 9 | EC_A19 | 100 | 14882.8 |
| 10 | EC_A21 | 100 | 1986.3 |
| 11 | EC_A22 | 100 | 1181.1 |
| 12 | EC_A43 | 100 | 6189.2 |
| 13 | EC_A70-1 | 100 | 4047.1 |
| 14 | EC_A78 | 100 | 23396.6 |
| 15 | EC_A79 | 100 | 12527.5 |
| 16 | EC_A83 | 100 | 7316.6 |
| 17 | EC_A84 | 100 | 2197.8 |
| 18 | EC_A85 | 100 | 7687.7 |
| 19 | EC_A86 | 100 | 18542.0 |
| 21 | EC_A87 | 100 | 7198.0 |
| 22 | EC_A88 | 100 | 17552.5 |
| 23 | EC_A89 | 100 | 6969.9 |
| 24 | EC_A91 | 100 | 9429.8 |
| 25 | EC_A92 | 100 | 2891.6 |
| 26 | EC_A93 | 100 | 6828.6 |
| 27 | EC_A96 | 100 | 15110.8 |
| 28 | EC_A97 | 100 | 7440.6 |
| 29 | EC_A98 | 100 | 11056.8 |
| 30 | EC_A99 | 100 | 7164.9 |
| 31 | EC_A100 | 100 | 8947.2 |
| 32 | EC_A101 | 100 | 4848.9 |
| 33 | EC_A102 | 100 | 8091.5 |

Figure 6:
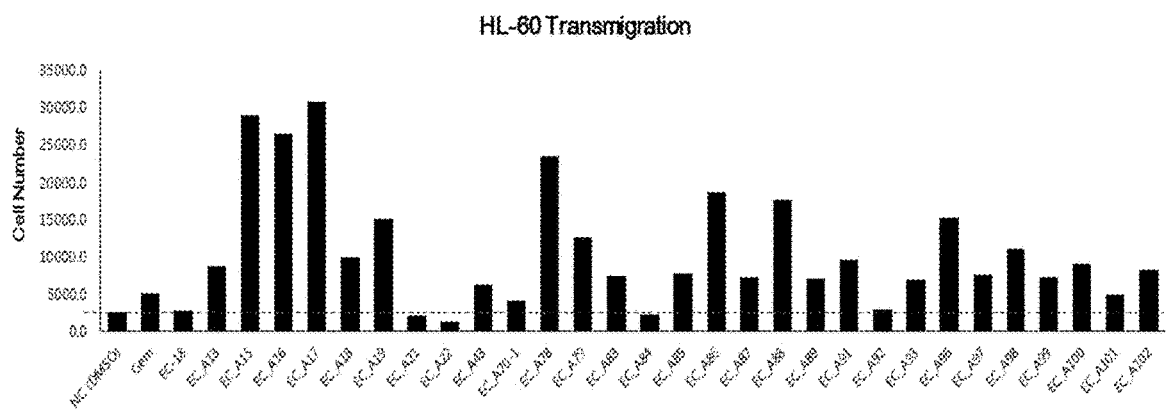
FIG. 6 is a graph showing the effect of the HL-60 cell line migration reduction of the conventional and diacylglycerol derivative compound according to the present invention.

As shown in Table 7 and FIG. 6, it was confirmed that when Gemcitabine, an anticancer drug, was treated in THP-1 cells, a neutrophil cell migration was increased by about twice compared to the negative control group (Experiment 2). When the EC-18 (PLAG) was treated, the migration of HL-60 cells was reduced to a degree similar to that of the negative control group (Experiment 3). Meanwhile, among the glycerol derivative compounds of the present invention, the compounds of A21, A22, A84, A92 were decreased the migration of cells similar to or more than the EC-18 (PLAG). In particular, it was confirmed that the compound of A 22 was reduced the migration of cell by about twice compared to the EC-18.

[Experimental Example 6] Infection Inhibition Test of Animal Model of Lung Infection with Bacteria For getting mice model whose lung are infected with bacteria, 12-week old Balb/c male mice were purchased from Koatech Corporation (South Korea) and maintained in certain pathogen-free facilities under moderate temperature and lights cycles. For obtain bacteria to induce lung infection, *Aeruginosa* K (PAK) of the genus *Psuedomonas* was incubated in LB broth or LB agar plate overnight at 37° C., and then the culture solution was centrifuged at 13,000×g for 2 minutes to obtain a bacterial pellet. Thereafter, the bacterial pellet was suspended in phosphate buffered saline (PBS), and the optical density of the serial dilution was measured and plated on an agar plate, so that bacterial inoculum having a colony forming unit (CFU) was obtained. A bacterial inoculum solution for infection was prepared at a concentration of $1\times10^5$ CFU per 20 μl, and the prepared PAK bacterial inoculum (1×105 CFU per mouse in 20 μl PBS) was administered to a total of 8 12-week-old Balb/c mice by nasal injection. Four of the PAK-administered groups were orally administered the compound of the present invention (EC_A21) at 250 mg/kg, and PBS was administered to the control group. After 4 hours, samples of bronchoalveolar lavage fluid (BALF) from *P. aeruginosa*-infected mice were collected, and the collected BALF samples were diluted 1:1000 with PBS. The diluted samples were plated on LB agar and then incubated overnight at 37° C. CFU levels in BALF were confirmed by measuring the number of surviving bacteria by a plate count method. The results are shown in Table 8, FIG. 7 and FIG. 8 below.

TABLE 8

| Example No. | Negative control group | PAK-infected group ($10^3$ CFU/ml) | PAK + glycerol derivative A21 treated group ($10^3$ CFU/ml) |
|---|---|---|---|
| 1 | 0 | 112.0 | 19.0 |
| 2 | 0 | 246.0 | 20.0 |
| 3 | 0 | 220.0 | 14.0 |
| 4 | 0 | 60.0 | 8.0 |
| average ± deviation | 0 | 160.0 ± 88.0 | 14.0 ± 6.0 |

Figure 7:
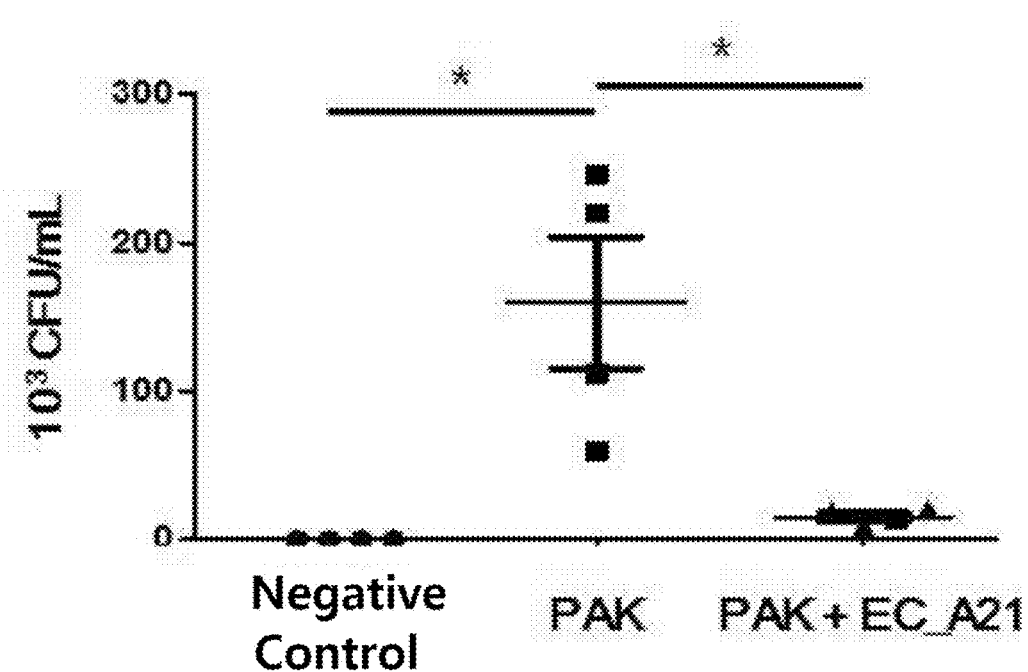
FIGS. 7 and 8 are a graph and photographs showing the results of an infection inhibition experiment in an animal model of bacterial lung infection of the glycerol derivative compound of the present invention.
Figure 8:
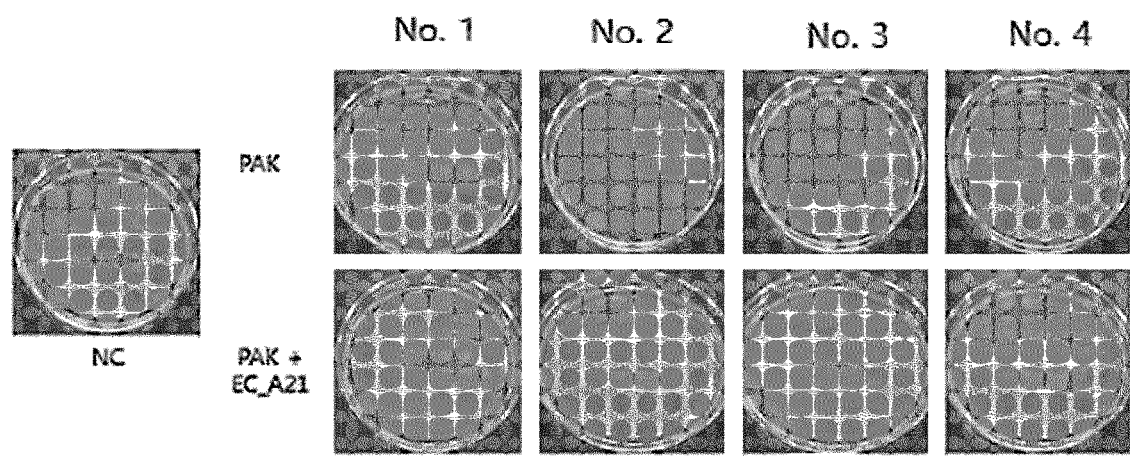

As shown in Table 8, FIG. 7 and FIG. 8, at the fourth hour after PAK administration, the bacterial CFU in the Pepo wash solution (BALF) increased rapidly.

However, among the glycerol derivatives of the present invention, when the A21 derivative, which significantly reduced neutrophil migration, and PAK, were administered together, the bacterial CFU in the pepo wash solution at the forth hour was significantly lower than that of the PAK alone group. The above results showed that the glycerol derivative compounds of the present invention was promoted the removal of bacteria in the early stages of infection in PAK-infected mice.

[Experimental Example 7] IL-4-Induced STAT6 Activity Reduction

In DMEM (Dulbecco Modified Eagle Medium, Hyclone, Thermo Scientific) medium to which 10% Fetal Bovine Serum was added, A549 cells were subcultured at a concentration of $1 \times 10^5$ cells/ml, and culture was conducted in a 5% $CO_2$ humidified incubator at 37° C. The cultured A549 cells were inoculated into a 48 well plate by $1 \times 10^5$ cells/ml and stabilized for 18 hours. Thereafter, pGL4-STAT6 reporter vector containing a STAT6 binding promoter portion was mixed with Attractene to induce complex formation at room temperature for 15 minutes. This complex was treated with the cells and then further incubated for 24 hours. Thereafter, the culture solution was treated with a glycerol derivative compounds of the type shown in Table 9 and 10 below for 1 hour, and then IL-4 (2 ng/ml or 10 ng/ml) was further incubated for 20 hours for STAT6 activity. Thereafter, the culture supernatant was removed for each well, and the remaining cells were lysed with a cell lysis buffer, and then cell lysate was recovered. 90 μl of luciferase reagent was mixed with 10 μl of the recovered cell lysate, and the degree of fluorescence was confirmed using a luminometer. The results are shown in Table 9, Table 10, FIG. 9 and FIG. 10 below.

TABLE 9

| Experiment | Sample | Concentration (μg/ml) | STAT6 activity_Luciferase activity (average ± deviation) |
|---|---|---|---|
| 1 | Negative control group | 0 | 8.5 ± 1.2 |
| 2 | IL-4 | 2 | 982.0 ± 38.7 |
| 3 | EC_18 | 100 | 462.5 ± 161.7 |
| 4 | EC_A13 | 100 | 1150.2 ± 44.9 |
| 5 | EC_A14 | 100 | 539.2 ± 40.3 |
| 6 | EC_A15 | 100 | 707.5 ± 51.3 |

TABLE 9-continued

| Experiment | Sample | Concentration (μg/ml) | STAT6 activity_Luciferase activity (average ± deviation) |
|---|---|---|---|
| 7 | EC_A16 | 100 | 964.5 ± 170.3 |
| 8 | EC_A17 | 100 | 476.2 ± 113.4 |
| 9 | EC_A18 | 100 | 1189.2 ± 174.7 |
| 10 | EC_A19 | 100 | 898.7 ± 115.9 |
| 11 | EC_A20 | 100 | 609.5 ± 197.0 |
| 12 | EC_A21 | 100 | 880.0 ± 50.0 |
| 13 | EC_A22 | 100 | 645.5 ± 111.4 |

TABLE 10

| Experiment | Sample | Concentration (μg/ml) | STAT6 activity_Luciferase activity (average ± deviation) |
|---|---|---|---|
| 1 | Negative control group | 0 | 11.5 ± 6.8 |
| 2 | IL-4 | 10 | 22846.2 ± 2157.3 |
| 3 | EC_18 | 100 | 18878.0 ± 500.8 |
| 4 | EC_A78 | 100 | 19208.7 ± 2129.6 |
| 5 | EC_A79 | 100 | 20037.7 ± 786.0 |
| 6 | EC_A83 | 100 | 18788.2 ± 2805.4 |
| 7 | EC_A85 | 100 | 19878.2 ± 4338.5 |
| 8 | EC_A86 | 100 | 18158.0 ± 3182.4 |
| 9 | EC_A87 | 100 | 17258.7 ± 3007.1 |
| 10 | EC_A88 | 100 | 17409.5 ± 1849.8 |
| 11 | EC_A89 | 100 | 18635.5 ± 846.4 |
| 12 | EC_A91 | 100 | 22036.0 ± 4089.4 |
| 13 | EC_A92 | 100 | 17237.2 ± 317.7 |
| 14 | EC_A93 | 100 | 15562.5 ± 900.7 |
| 15 | EC_A94 | 100 | 14677.5 ± 2168.7 |
| 16 | EC_A95 | 100 | 13649.0 ± 7369.3 |
| 17 | EC_A96 | 100 | 14593.2 ± 2168.7 |
| 18 | EC_A97 | 100 | 16787.0 ± 4102.6 |
| 19 | EC_A98 | 100 | 14727.2 ± 129.2 |
| 20 | EC_A99 | 100 | 17407.0 ± 1347.6 |
| 21 | EC_A100 | 100 | 14212.0 ± 1008.8 |
| 22 | EC_A101 | 100 | 19438.7 ± 580.2 |
| 23 | EC_A102 | 100 | 18719.2 ± 2558.5 |

Figure 9:
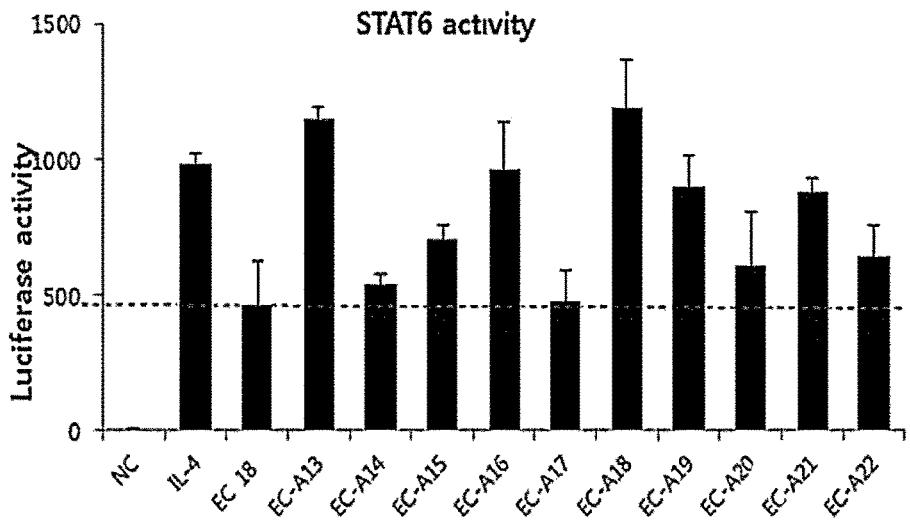
FIGS. 9 and 10 are graphs showing the effect of STAT6 activity reduction of the conventional and diacylglycerol derivative compound according to the present invention.
Figure 10:
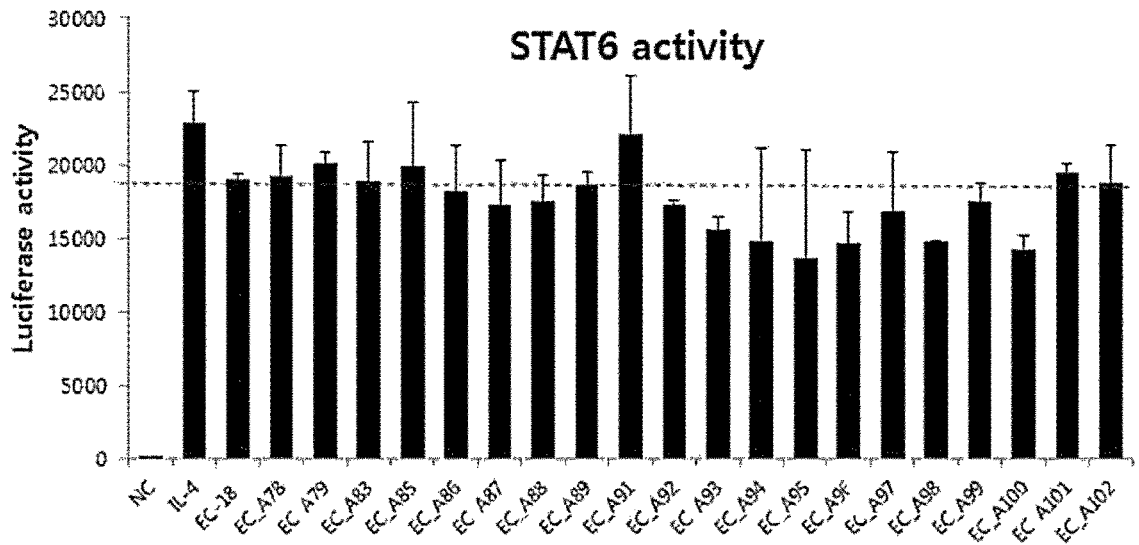

As shown in Table 9, Table 10, FIG. 9 and FIG. 10, it was confirmed that when IL-4 was treated in A549 cells, the STAT6 activity was increased according to amount of the treated IL-4 by about 120 to 2000 times compared to the negative control group (Experiment 2). When the EC-18 (PLAG) was treated, the STAT6 activity was reduced by about 20% to 50% (Experiment 3). Meanwhile, it was confirmed that among the glycerol derivative compounds of the present invention, the compounds of A14, A15, A17, A20, A21, A22, A78, A79, A83, A85, A86, A87, A88, A89, A92, A93, A94, A95, A96, A97, A98, A99, A100, A101, A102 were decreased the STAT6 activity similar to the EC-18 (FLAG).

[Experimental Example 8] PKC Activator-Induced IL-4 Secretion Reduction

In DMEM (Dulbecco Modified Eagle Medium, Hyclone, Thermo Scientific) medium to which 10% Fetal Bovine Serum was added, EL-4 cells, a mouse lymphoma family, were subcultured at a concentration of $1 \times 10^5$ cells/ml, and culture was conducted in a 5% $CO_2$ humidified incubator at 37° C. The cultured EL-4 cells were inoculated into a 48 well plate by $5 \times 10^4$ cells/ml and stabilized for 30 hours. Then, the culture solution was treated with a glycerol derivative compounds of the type shown in Table 11 and 12 below for 2 hours. Thereafter, it were treated with 0.5 µg/ml of PKC activator (p10, some kind of PMA) of a cell stimulator, and subsequent further incubation were conducted for 18 hours. Thereafter 0.5 ml of the culture supernatant was collected for each well and centrifuged (at 3000 rpm, 5 minutes) to recover the supernatant. The IL-4 level in the recovered supernatant was measured according to the manual provided by the Mouse IL-4 ELISA set (BD Biosciences). The day before ELISA was carried out, the IL-4 capture antibody was diluted in phosphate buffered saline, coated on a microwell, and then stored at 4° C. overnight. Each well was washed three times with a buffer solution and then blocked with 2% Bovine Serum Albumin (BSA) for 1 hour at room temperature. After washing with buffer solution three times, 100 µl of sample was dispensed into each well and left at room temperature for 2 hours. Detection antibody which was washed 3 times with washing buffer solution and diluted was dispensed into each well and allowed to react at room temperature for 1 hour and left at room temperature for 1 hour. Thereafter, the secondary HRP conjugated antibody was reacted at room temperature for 30 minutes, washed three times with buffer solution, and treated with 50 µl of stop solution for each well, and then the optical density was measured at 450 nm with an ELISA microplate leader. The results of the measured expression reduction rate (IL-6 concentration) were shown in Table 11, Table 12, FIG. 11 and FIG. 12 below.

TABLE 11

| Experiment | Sample | Concentration (µg/ml) | IL-4 concentration (pg/µl, average ± deviation) |
| --- | --- | --- | --- |
| 1 | Negative control group | 0 | 1.5 ± 1.2 |
| 2 | PKC activator | 1 | 910.6 ± 25.7 |
| 3 | EC-18 | 100 | 662.4 ± 42.4 |
| 4 | EC__A20 | 100 | 194.2 ± 47.5 |
| 5 | EC__A21 | 100 | 488.8 ± 46.2 |
| 6 | EC__A57 | 100 | 745.6 ± 8.35 |
| 7 | EC__A70-1 | 100 | 865.6 ± 127.9 |

TABLE 12

| Experiment | Sample | Concentration (µg/ml) | IL-4 concentration (pg/µl, average ± deviation) |
| --- | --- | --- | --- |
| 1 | Negative control group | 0 | −12.5 ± 3.2 |
| 2 | PKC activator | 1 | 628.8 ± 0.0 |
| 3 | EC-18 | 100 | 429.2 ± 7.0 |
| 4 | EC__A78 | 100 | 557 ± 11.5 |
| 5 | EC__A79 | 100 | 527 ± 17.9 |
| 7 | EC__A83 | 100 | 637.9 ± 14.1 |
| 8 | EC__A84 | 100 | 615.6 ± 25.0 |
| 9 | EC__A85 | 100 | 485.1 ± 19.2 |
| 10 | EC__A86 | 100 | 476.0 ± 2.5 |
| 11 | EC__A87 | 100 | 511.0 ± 0.6 |
| 12 | EC__A88 | 100 | 654.7 ± 0.6 |
| 13 | EC__A89 | 100 | 620.1 ± 22.4 |
| 14 | EC__A91 | 100 | 446.0 ± 16.7 |
| 15 | EC__A92 | 100 | 498.3 ± 45.6 |
| 16 | EC__A93 | 100 | 507.9 ± 3.85 |
| 17 | EC__A94 | 100 | 523.8 ± 62.3 |
| 18 | EC__A95 | 100 | 680.1 ± 12.2 |
| 19 | EC__A96 | 100 | 582.9 ± 17.3 |
| 20 | EC__A97 | 100 | 541.5 ± 20.5 |
| 21 | EC__A98 | 100 | 584.2 ± 50.1 |
| 22 | EC__A99 | 100 | 553.3 ± 39.8 |
| 23 | EC__A100 | 100 | 539.7 ± 6.4 |
| 24 | EC__A101 | 100 | 634.7 ± 3.21 |
| 25 | EC__A102 | 100 | 775.1 ± 11.5 |

Figure 11:
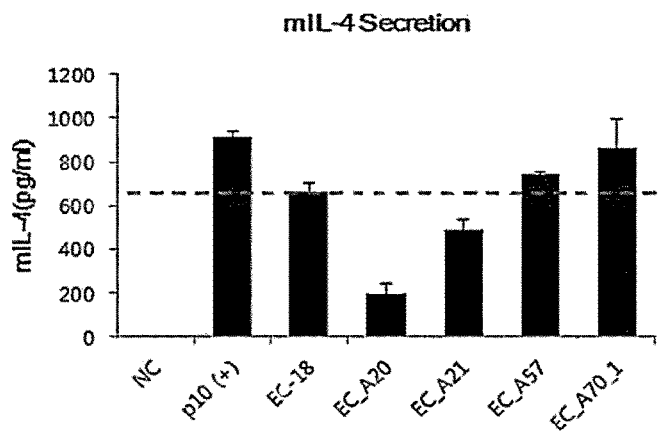
FIGS. 11 and 12 are graphs showing the effect of IL-4 secretion reduction of the conventional and diacylglycerol derivative compound according to the present invention.
Figure 12:
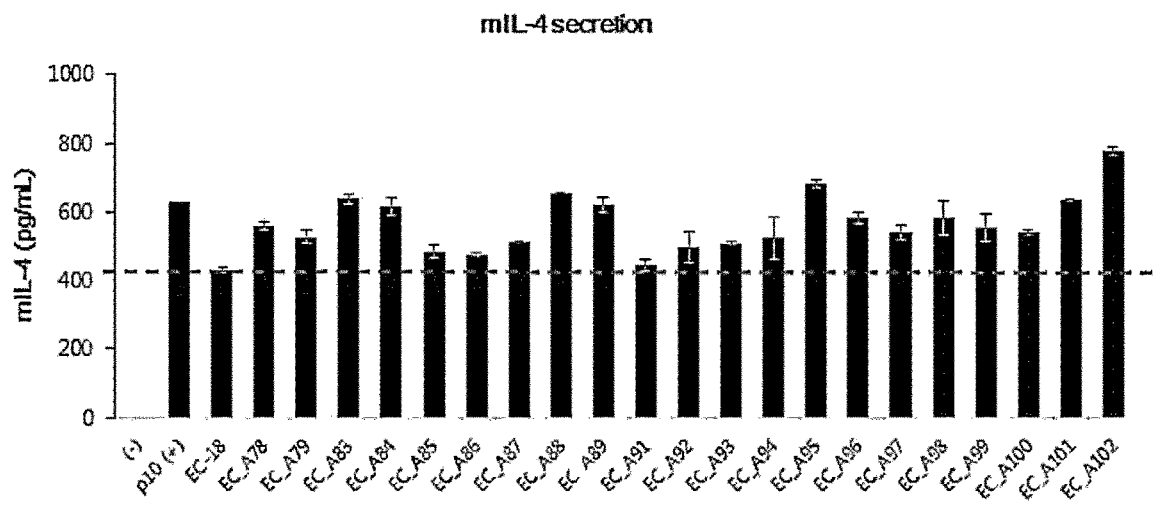

As shown in Table 11, Table 12, FIG. 11 and FIG. 12, it was confirmed that when PKC activator were treated in mouse EL-4 cells, the secretion of IL-4 cytokine was rapidly increased by compared to the negative control group (Experiment 2). when EC-18 (PLAG) compound was treated, the IL-4 expression was decrease about 20% to 60% (Experiment 3). Meanwhile, among the glycerol derivative compounds of the present invention, the compounds of A85, A86, A87, A91, A92, A93 were decreased the secretion of IL-4 cytokines by about 20% to a degree similar to EC-18 (PLAG). In particular, it was confirmed that the compounds of A20 and A21 were decreased IL-4 expression by up to 80% much more strongly than that of EC-18.

The invention claimed is:

1. A 1,2-diacylglycerol compound represented by following Chemical formula 2,

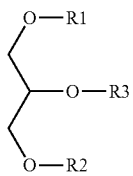

[Chemical formula 2]

wherein in Chemical formula 2, R1 is octanoyl, lauroyl, decanoyl or palmitoyl, R3 is butyryl, 2-methylbutyryl, pivaloyl or linoleoyl, and R2 is methyl group, ethyl group, propyl group or isopropyl group.

2. An immunomodulator comprising the 1,2-diacylglycerol compound represented by following Chemical formula 2 as an active ingredient,

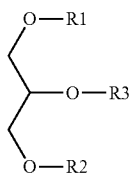

[Chemical formula 2]

wherein in Chemical formula 2, R1 is octanoyl, lauroyl, decanoyl or palmitoyl, R3 is butyryl, 2-methylbutyryl, pivaloyl or linoleoyl, and R2 is methyl group, ethyl group, propyl group or isopropyl group.

3. The immunomodulator of claim 2, wherein the 1,2-diacylglycerol compound inhibits the overexpression of one or more inflammatory cytokines selected from the group consisting of IL-4, IL-6, and CXCL8 (IL-8).

4. The immunomodulator of claim 2, wherein the 1,2-diacylglycerol compound treats immune disease selected from the group consisting of bacterial or viral infections, acute and chronic inflammatory lung diseases, pneumonia, autoimmune disease, allergic disease and cancer.

5. The immunomodulator of claim 2, wherein an amount of the 1,2-diacylglycerol compound is 0.0001 to 100.0% by weight.

6. A health functional food composition for immunity enhancement, comprising the 1,2-diacylglycerol compound represented by following Chemical formula 2 as an active ingredient,

[Chemical formula 2]

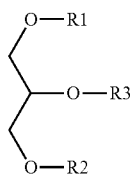

wherein in Chemical formula 2, R1 is octanoyl, lauroyl, decanoyl or palmitoyl, R3 is butyryl, 2-methylbutyryl, pivaloyl or linoleoyl, and R2 is methyl group, ethyl group, propyl group or isopropyl group.

7. A method for immunity regulation comprising administering to a subject the immunomodulator according to claim 2.

8. A method for immunity regulation comprising administering to a subject the immunomodulator according to claim 3.

9. A method for immunity regulation comprising administering to a subject the immunomodulator according to claim 4.

10. A method for immunity regulation comprising administering to a subject the immunomodulator according to claim 5.

* * * * *